United States Patent
Garibaldi et al.

(10) Patent No.: US 8,806,359 B2
(45) Date of Patent: Aug. 12, 2014

(54) WORKFLOW DRIVEN DISPLAY FOR MEDICAL PROCEDURES

(75) Inventors: Jeffrey M. Garibaldi, St. Louis, MO (US); Walter M. Blume, St. Louis, MO (US); Nathan Kastelein, St. Louis, MO (US); Raju R. Viswanathan, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 1234 days.

(21) Appl. No.: 11/801,123

(22) Filed: May 8, 2007

(65) Prior Publication Data

US 2008/0064933 A1 Mar. 13, 2008

Related U.S. Application Data

(63) Continuation of application No. 11/670,919, filed on Feb. 2, 2007.

(60) Provisional application No. 60/871,774, filed on Dec. 22, 2006, provisional application No. 60/842,633, filed on Sep. 6, 2006.

(51) Int. Cl.
*G06F 3/048* (2013.01)

(52) U.S. Cl.
USPC .......................................................... 715/771

(58) Field of Classification Search
USPC .................. 715/705, 737, 740, 761, 767, 771
See application file for complete search history.

(56) References Cited

U.S. PATENT DOCUMENTS

| | | | |
|---|---|---|---|
| 5,654,864 A | 8/1997 | Ritter et al. |
| 5,931,818 A | 8/1999 | Werp et al. |
| 6,014,580 A | 1/2000 | Blume et al. |
| 6,015,414 A | 1/2000 | Werp et al. |
| 6,128,174 A | 10/2000 | Ritter et al. |
| 6,148,823 A | 11/2000 | Hastings |
| 6,152,933 A | 11/2000 | Werp et al. |
| 6,157,853 A | 12/2000 | Blume et al. |
| 6,212,419 B1 | 4/2001 | Blume et al. |
| 6,241,671 B1 | 6/2001 | Ritter et al. |
| 6,292,678 B1 | 9/2001 | Hall et al. |
| 6,296,604 B1 | 10/2001 | Garibaldi et al. |
| 6,298,257 B1 | 10/2001 | Hall et al. |
| 6,304,768 B1 | 10/2001 | Blume et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,475,223 B1 | 11/2002 | Werp et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |

(Continued)

*Primary Examiner* — Enrique Iturralde
(74) *Attorney, Agent, or Firm* — Harness, Dickey & Pierce, P.L.C.

(57) ABSTRACT

A display for operating a plurality of separate computer systems, each having a visual display. The display includes comprising a composite display, a video system for receiving display input from each of the plurality of separate computer systems and displaying it on the composite display, a processor which controls the content of the composite display based upon a planned procedure workflow.

9 Claims, 20 Drawing Sheets

(56) References Cited

U.S. PATENT DOCUMENTS

| | | |
|---|---|---|
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al |
| 2001/0038683 A1 | 11/2001 | Ritter et al. |
| 2002/0019644 A1 | 2/2002 | Hastings et al. |
| 2002/0100486 A1 | 8/2002 | Creighton, IV et al. |
| 2002/0177789 A1 | 11/2002 | Ferry et al. |
| 2003/0125752 A1 | 7/2003 | Werp et al. |
| 2004/0002643 A1 | 1/2004 | Hastings et al. |
| 2004/0006301 A1 | 1/2004 | Sell et al. |
| 2004/0019447 A1 | 1/2004 | Shachar |
| 2004/0030244 A1 | 2/2004 | Garibaldi et al. |
| 2004/0064153 A1 | 4/2004 | Creighton, IV et al. |
| 2004/0068173 A1 | 4/2004 | Viswanathan |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0199074 A1 | 10/2004 | Ritter et al. |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0033162 A1 | 2/2005 | Garibaldi et al. |
| 2005/0043611 A1 | 2/2005 | Sabo et al. |
| 2005/0065435 A1 | 3/2005 | Rauch et al. |
| 2005/0096589 A1 | 5/2005 | Shachar |
| 2005/0113628 A1 | 5/2005 | Creighton, IV et al. |
| 2005/0113812 A1* | 5/2005 | Viswanathan et al. ............ 606/1 |
| 2005/0119556 A1 | 6/2005 | Gillies et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2005/0273130 A1 | 12/2005 | Sell |
| 2006/0004382 A1 | 1/2006 | Hogg et al. |
| 2006/0009735 A1 | 1/2006 | Viswanathan et al. |
| 2006/0025676 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036125 A1 | 2/2006 | Viswanathan et al. |
| 2006/0036163 A1 | 2/2006 | Viswanathan |
| 2006/0036213 A1 | 2/2006 | Viswanathan et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0061445 A1 | 3/2006 | Creighton, IV |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2006/0145799 A1 | 7/2006 | Creighton, IV |
| 2006/0270915 A1 | 11/2006 | Ritter et al. |
| 2006/0270948 A1 | 11/2006 | Viswanathan et al. |
| 2006/0278248 A1 | 12/2006 | Viswanathan |
| 2007/0016010 A1 | 1/2007 | Creighton, IV et al. |
| 2007/0016131 A1 | 1/2007 | Munger et al. |
| 2007/0019330 A1 | 1/2007 | Wolfersberger |
| 2007/0021731 A1 | 1/2007 | Garibaldi et al. |
| 2007/0021742 A1 | 1/2007 | Viswanathan |
| 2007/0021744 A1 | 1/2007 | Creighton, IV |
| 2007/0030958 A1 | 2/2007 | Munger |
| 2007/0032746 A1 | 2/2007 | Sell |
| 2007/0038064 A1 | 2/2007 | Creighton, IV |
| 2007/0038065 A1 | 2/2007 | Creighton, IV et al. |
| 2007/0038074 A1 | 2/2007 | Ritter et al. |
| 2007/0038410 A1 | 2/2007 | Tunay |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0055130 A1 | 3/2007 | Creighton, IV |
| 2007/0060829 A1 | 3/2007 | Pappone |
| 2007/0060916 A1 | 3/2007 | Pappone |
| 2007/0060962 A1 | 3/2007 | Pappone |
| 2007/0060966 A1 | 3/2007 | Pappone |
| 2007/0060992 A1 | 3/2007 | Pappone |
| 2007/0062546 A1 | 3/2007 | Viswanathan et al. |
| 2007/0062547 A1 | 3/2007 | Pappone |
| 2007/0073288 A1 | 3/2007 | Hall et al. |
| 2007/0088197 A1 | 4/2007 | Garibaldi et al. ............ 600/114 |
| 2007/0159457 A1 | 7/2007 | Arthur ........................ 345/156 |

* cited by examiner

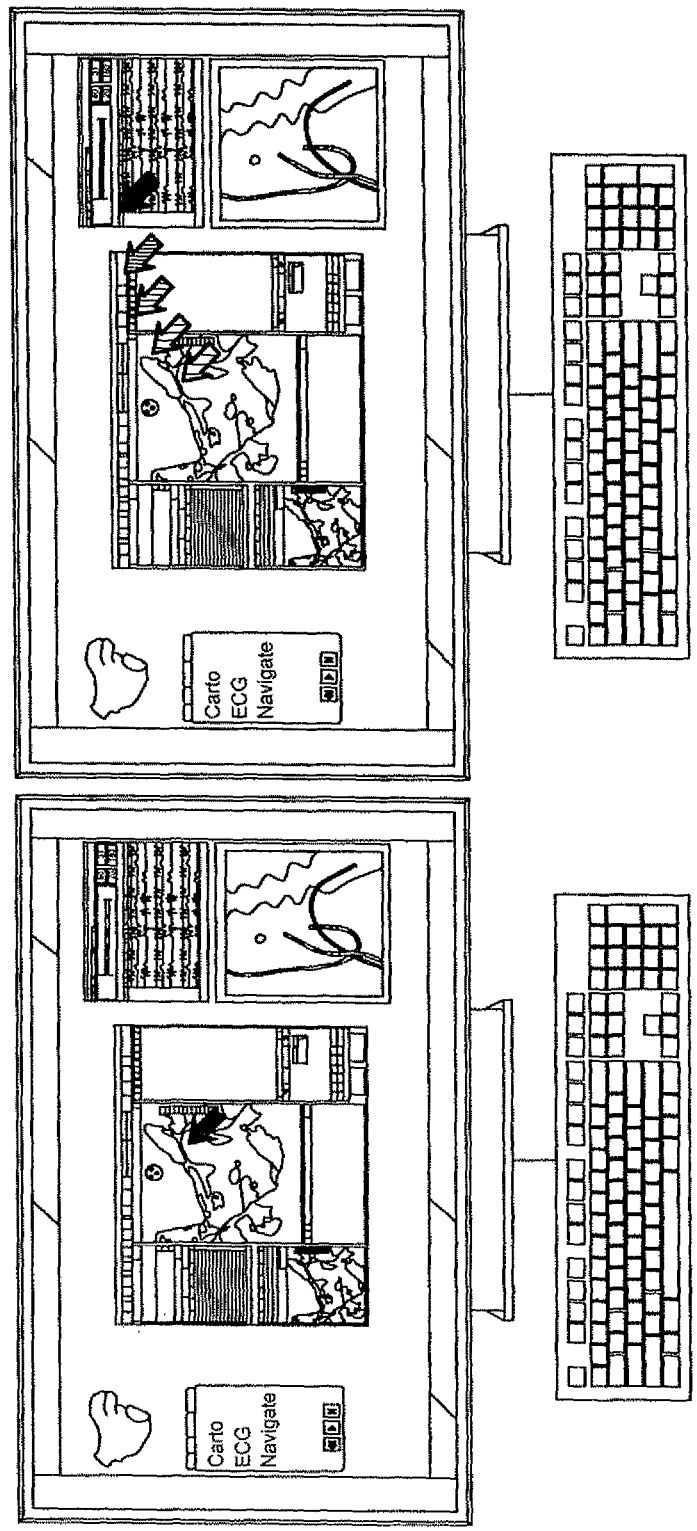

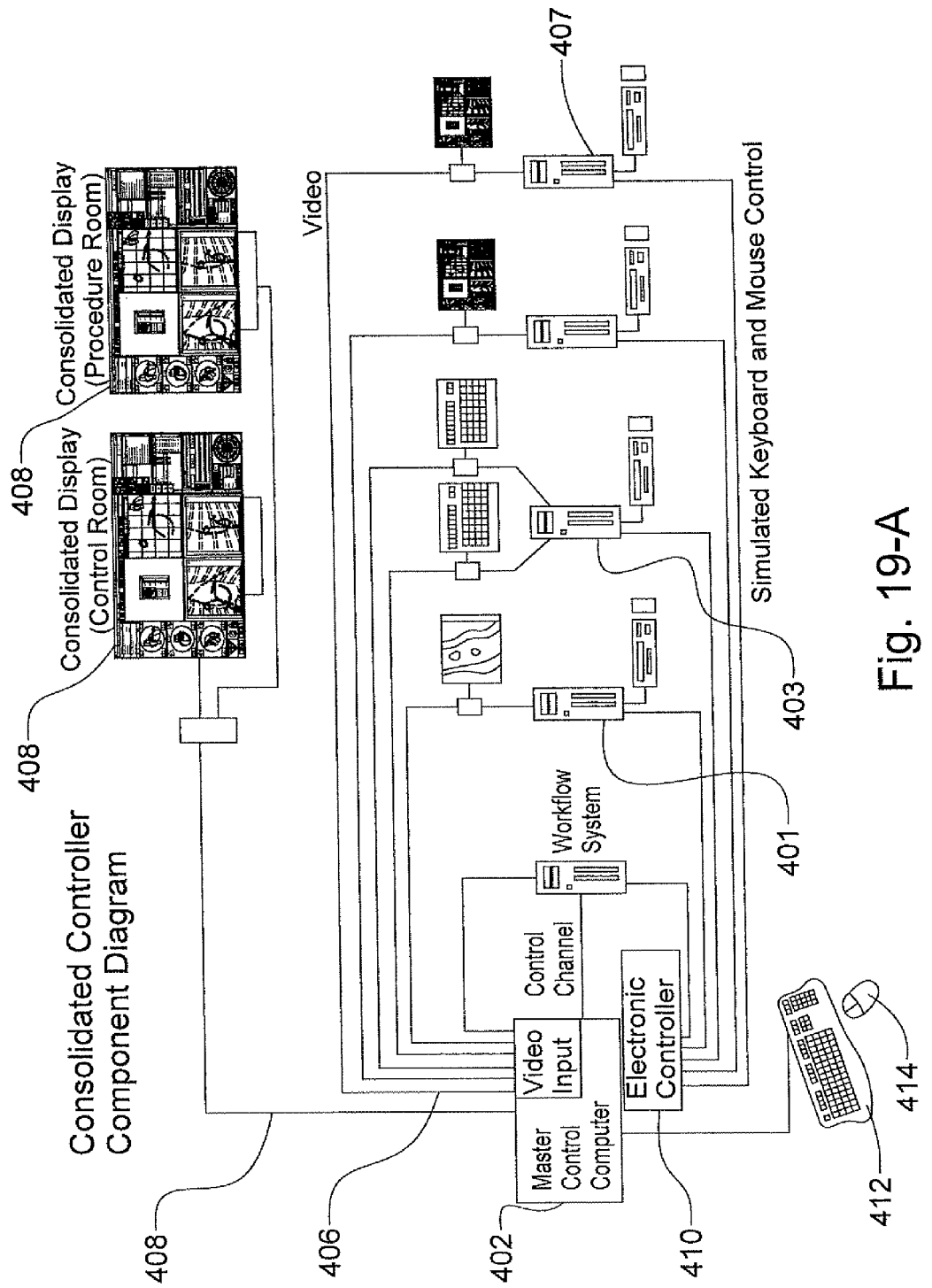
Fig. 19-A

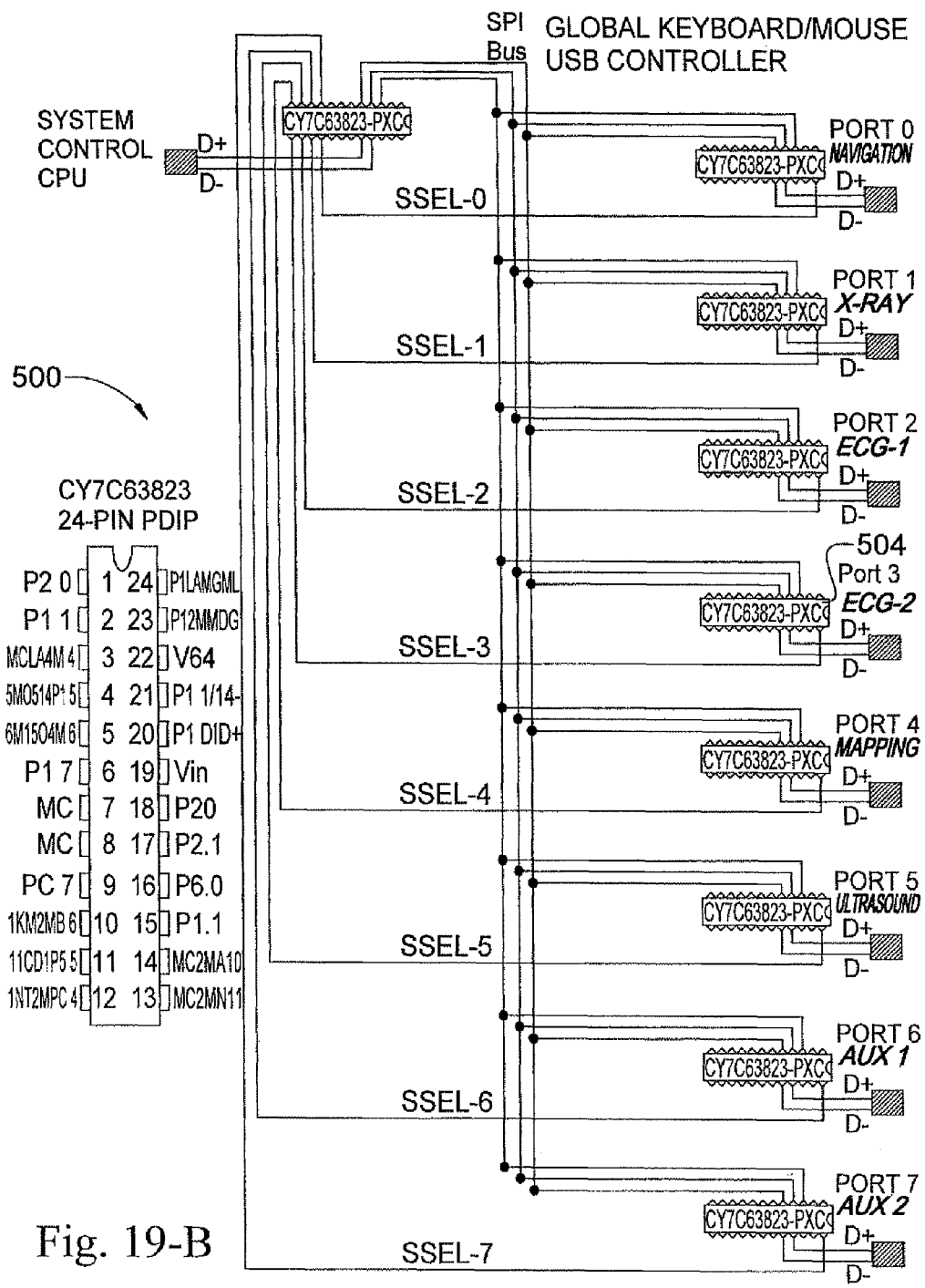
Fig. 19-B

WORKFLOW DRIVEN DISPLAY FOR MEDICAL PROCEDURES

CROSS-REFERENCE TO RELATED APPLICATIONS

This application is a continuation of U.S. patent application Ser. No. 11/670,919, filed Feb. 2, 2007, which claims benefit of U.S. Provisional Patent Application 60/871,774, filed Dec. 22, 2006, and U.S. Provisional Patent Application 60/842,633, filed Sep. 6, 2006, all of which are incorporated by reference herein.

BACKGROUND

This invention relates to a consolidated user interface systems and methods and in particular, to an interface for operating multiple medical systems.

Many of today's most advanced and effective diagnostic and therapeutic procedures involve the coordinated use of multiple separate medical systems. Each of these separate medical systems may include its own visual display and its own input device. As a result, the visual displays and input devices can take up valuable space in the procedure room, as they must be placed in position for convenient access and use. These multiple displays and input device also pose a risk of confusion among the various displays and input devices.

SUMMARY

Generally, the present invention relates to the seamless, workflow-driven operation of multiple separate medical systems. Embodiments of the present invention provide systems and methods for the operation of two or more medical systems, each having a visual display and standard input devices.

Generally a preferred embodiment of a system for controlling multiple separate medical systems comprises a display with an active display portion and an inactive display portion, an input device, and a controller for selecting one of the medical systems whose visual display is displayed on the active region of the display, and which is controlled by the input device. For the purpose of this disclosure, "active" means that the corresponding medical system or remote computer has been selected for both inputs and outputs. The controller selects the medical system at least in part according to a predetermined routine based upon the procedure being performed. Alternatively or additionally, the controller selects the medical system at least in part based upon information from at least one of the medical system. Alternatively or additionally, the controller selects the medical system at least in part based upon user selection.

Generally a preferred embodiment of a method for controlling multiple separate medical systems comprises displaying the visual display output of one of the medical systems on a dedicated active display area, and displaying the visual display output of at least one non-selected medical systems on an inactive display area; communicating commands from at least one input device to the medical system whose visual display output is being displayed on the active area, and actively switching the medical system whose visual display output is displayed on the active area. The medical system whose visual display output is displayed on the active display area is selected at least in part according to a predetermined order based upon the type of procedure being performed with the medical systems. Alternatively or additionally, the medical system selected to have its visual display output displayed on the active display is selected at least in part based upon input received from at least some of the medical systems. Alternatively or additionally the medical system selected to have its visual display output displayed on the active display is selected at least in part based upon user input.

In another preferred embodiment, multiple active displays of multiple medical systems are provided on the composite display, and the movement of a user input device such as a computer mouse is seamlessly tracked by a processor and actively assigned to the appropriate medical system based on the location of the mouse within the composite display.

Embodiments of this invention provide systems and methods facilitating the operation of multiple separate medical systems, simplifying the procedure control site and reducing the risk of confusion.

BRIEF DESCRIPTION OF DRAWINGS

FIGS. 18A and 18B are views of the composite display, illustrating the use of a single input device to control multiple systems depending upon the positioning of the cursor; and FIGS. 19A and 19B show a diagram of a number of components and systems networked via a USB controller.

Corresponding reference numerals indicate corresponding parts throughout the several views of the drawings.

DETAILED DESCRIPTION

Figure 1:
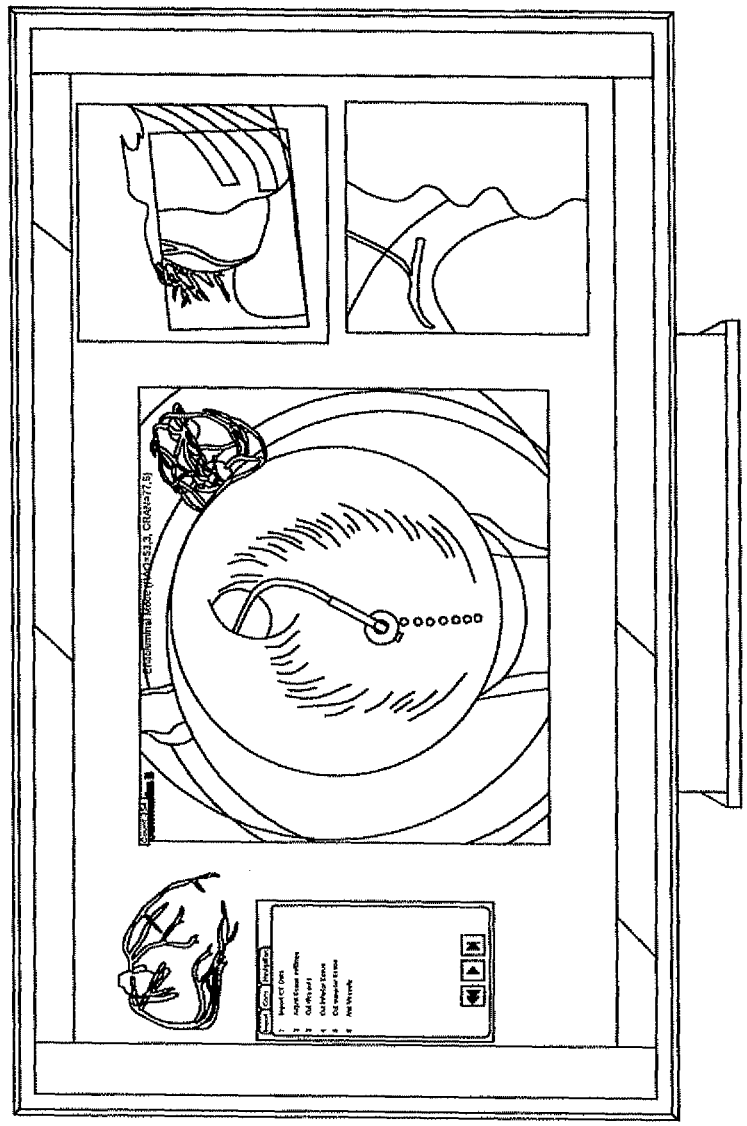
FIG. 1 is a schematic view of a preferred embodiment of a system for controlling multiple medical devices in accordance with the principles of this invention.

A preferred embodiment of a system for controlling multiple medical systems is indicated generally as 20 in FIG. 1. As shown in FIG. 1, the system 20 is adapted for use in controlling two or more separate medical systems. For example as shown in FIG. 1 the system 20 is adapted for controlling three separate medical systems, a remote navigation system 22, a localization system 24, and an X-ray imaging system 26. While the preferred embodiment is described in the context of three systems 22, 24, and 26, the invention is not so limited, and can be used with any number of medical systems, and furthermore can be used with additional or different medical systems such as an Ultrasound imaging system or an ECG recording system. Each of these separate medical systems preferably generates visual display data, and preferably also is adapted to receive input commands from an input device. Most of these separate medical systems are PC or computer based, with a conventional monitor, and a conventional input device such a keyboard and mouse, track ball, joy stick, etc.

In this preferred embodiment the system 20 includes a display 28, having an active display area 30 and a passive display area 32. The active and passive display areas 30 and 32 can be dedicated portions of a single display device, or they can be dynamically determined portions of a single display device, or they can be portions of separate display devices, which are preferably integrated together.

In this preferred embodiment the system 20 also includes at least one input device, such as a keyboard 34 and/or a mouse 36. The system 20 can also include additional or different input devices such as track balls, joysticks, haptic devices, touch screens, etc.

In this preferred embodiment the system 20 also includes a controller 38, which in this preferred embodiment includes a computer, such as PC 40. The computer is programmed to display the visual display data from a selected one of the medical systems (e.g. one of systems 22, 24, and 26) on the active area 30 of the display 28. The computer is also programmed to provide control signals from the input devices (e.g. keyboard 34 and mouse 36) to the selected medical system, so that the input devices control the medical system whose visual display data is displayed on the active display area 30 of the display 28. This helps eliminate confusion in operating the separate medical systems in the course of a procedure.

In this preferred embodiment the computer is preferably programmed to intelligently select the medical system based at least in part upon a predetermined routine for the medical procedure being performed. Thus, for example, some identification of the medical procedure being performed is provided to the computer, and the computer then selects the medical system to display in the active display area 30 of the display 28. For example this selection can be made based on the time since the start of the procedure, based upon indications of completion of various phases of the procedure either obtained from the various medical systems or from the user. For example after a particular action or command using one medical system, the computer may be programmed to automatically select another medical system. Alternatively or in addition, the computer may select the medical system at least in part based upon information received from the various medical systems. For example if the computer receives an alarm from a particular system, it might automatically select that system to facilitate the user's response to the alarm. Alternatively or in addition, the computer may select the medical system at least in part based upon information received from the user, including an express instruction to switch to a different medical system.

In particular the computer can be programmed to select the medical system based at least in part on a predetermined routine for a given medical procedure, and can take into account signals, including emergency signals, from the various medical systems being used, as well as inputs from the user reflecting the starting or completion of various phases or steps of the procedure, and specific requests to select a specific medical system.

Figure 2:
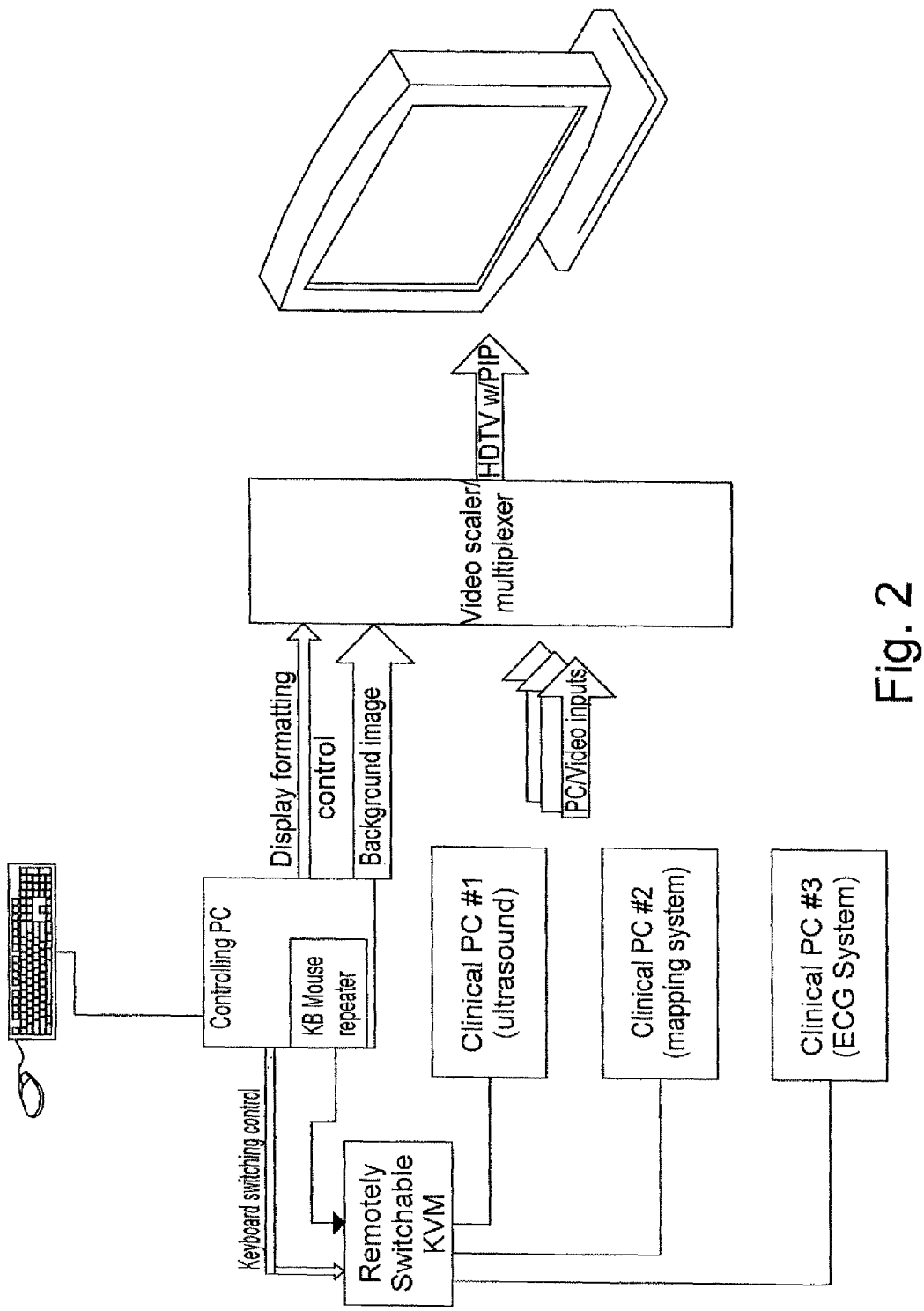
FIG. 2 is an elevation view of an example display of a system for controlling multiple medical devices in accordance with the principles of this invention.

As shown in FIG. 2, the active display portion 30 of the display 20 is preferably more prominent, for example in size and in location, than the inactive display portions 32. Thus it is immediately apparent what system is being actively displayed, and what system will be controlled by the use of the input devices (e.g. keyboard 34 and mouse 36). When the computer automatically changes selection of the medical system, there is preferably some sort of indication prior to the switch, and preferably some visible and/or audible signal at the switch. Furthermore, in one embodiment the input devices (e.g. keyboard 34 and mouse 36) may be temporarily locked out just prior to the switch until just after the switch, to reduce the risk that commands intended for one system are communicated to a different system.

The computer 40 can be programmed to prompt the user through a predetermined sequence of steps to conduct the procedure, the program automatically changing the selected medical system as the user responds to the on screen prompts, thereby automatically passing control of appropriate medical system to the keyboard 34 and mouse 36 (or other input devices) at the appropriate times. A portion of the display 28 can be dedicated to displaying prompts, or the prompts can be dynamically allocated.

For example a Clinical Workflow Manager program can be run on the computer 40 to direct the user to perform the steps necessary to perform the procedure, such as setting up an imaging, localization, and magnetic navigation systems for performing a procedure with magnetically navigated devices, and to make the systems required to perform the procedure accessible to the user via the system 20, and in particular the display 28 and the keyboard 34 and mouse 36.

The Clinical Workflow Manager Program might begin with a prompt on the display 28 to "Import Pre-Op image" or similar designation. When the user selects this, a Pre-Op window is opened, and a dialog box enables selection of the appropriate image. The image is loaded into the Pre-Op window. A prompt on the display 28 then prompts the user to move to the next step of acquiring a first X-ray image for registration.

During the acquisition of the first X-ray image for registration the user takes an X-ray image, and the active portion 30 of the display 28 displays the same image as the X-ray monitor. The x-ray system controls (zoom level, frame rate, window width, window level, etc.) are available on this "Live X-ray" display using the keyboard 34, mouse 36, or other input devices. As the user moves a cursor across this active portion 30 of the display 28 with the mouse 36, mouse movements are suitably scaled by the processor and fed to the x-ray system computer. Mouse clicks are also fed to the x-ray system computer. Thus X-ray system control settings may be changed if desired. When the user presses the X-ray foot switch to acquire an X-ray image, the user can directly observe the image on the active portion 30 of the display. The image is automatically stored to a separate "Reference X-ray" window when the mouse cursor is in the appropriate display area on the composite display corresponding to the X-ray system.

The Clinical Workflow Manager can then display a prompt on the display 28 to prompt the user to move to the next step of acquiring a second X-ray image for registration, the second x-ray image possibly being acquired at a different angle with respect to the patient. The x-ray system controls are accessible to the user from the "Live X-ray" window. When the second image is also selected, the Clinical Workflow Manager can then display a prompt on the display 28 to move to the next step of marking landmarks on the pair of X-ray images. A pair of x-ray images is displayed to the user on the active portion 30 of the display. After the user marks a set of corresponding points on the two images (thus defining a set of 3D points through epipolar geometry) using the keyboard 34 and mouse 36, the Clinical Workflow Manager can then display a prompt on the display 28 to select corresponding points on the Pre-Op image. The Clinical Workflow Manager can then display the Pre-Op image in the active portion 30 of the display 28. The user may rotate and translate the Pre-Op image as desired and select a set of landmarks. The landmarks can be matched with the corresponding set of X-ray landmarks from the previous step and the system effects a registration between the Pre-Op image and X-ray coordinates.

The Clinical Workflow Manager can then display a prompt on the display 28 to start Auto Map moves (apply preset field sequence, etc.) and switch the localization/mapping system display to the active portion 30 of the display 28. A sequence of moves is made and the user may move the mouse 36 to select and "freeze" points as one would typically do with a localization system in order to create an anatomical/ECG map. Mouse moves made on (or with reference to) the action portion 30 of the display 28 are suitably scaled and fed to the localization system computer, so that localization user interface tools can be accessed and used via system 20.

The mapping process continues until a complete or suitable anatomical map is obtained. The Pre-Op image may at any time be displayed as well upon user selection, so that anatomical targets can be selected from this image as locations to drive the catheter to (in order to further refine a map, for instance). This sequence outlines a mapping procedure that can be carried out with the system 20 coordinating separate imaging and localization and navigation systems. Although this sequence demonstrates an implementation with user selected screen displays on the system 20, other variations can consist entirely of an automated selection of displays (for instance: (i) as soon as an X-ray is transferred, the computer picks the next window/system to display, or (ii) instead of prompting the user to select the next display as in the above, the processor directly switches the display as appropriate), or a combination of automatically selected and user selected displays at various steps. Likewise, the displays of various systems such as Localization system, ECG system, blood pressure monitoring system, X-ray, Ultrasound or other imaging system, remote navigation system, and so on can be displayed on the Consolidated UI in various sequences as appropriate for the procedure.

Operation

In the preferred embodiment shown in FIG. 1, a single keyboard 34 and mouse 36 is attached to the controlling PC 40. This PC 40 produces a background image output to a video output that is combined with other clinical video streams by a Video scaler/multiplexer 42. The scaler multiplexer does the image processing necessary to produce an integrated display. An example of an available video scaler/multiplexer is the TVOne C2-7100 w/RS-232 control. It provides two programmable PIP (Picture in picture) windows overlaid on a main window and accepts multiple DVI and VGA inputs with an HDTV output.

A software program on the controlling PC 40 monitors the keyboard 34 and mouse 36 and passes information on as necessary to the remotely switchable kvm 44. The remotely switchable kvm 44 routes keystrokes to the appropriate medical system computer as commanded by the controlling PC. An example of a remote KVM that could do this is the Black Box KV3108SA-R5, 8 port controllable KVM.

The medical systems (e.g. systems 22, 24, and 26) can have their own mouse/keyboards that serve as backup controls. These could be attached via keyboard splitter and mouse splitter cables.

Of course the system 20 does not have to use a PC 40, and instead any device capable of producing a video image could be substituted. The computer would need to at least have a microprocessor with some software. Any clinical video producing device that could be controlled by a keyboard/mouse would be plugged into the KVM. It is possible that some medical systems will only produce video display data, and not accept inputs. These devices could nonetheless be integrated with the system 20, and displayed at appropriate times on the active display area 30 of the display 28, even though the input devices do not provide any control signals.

Figure 3:
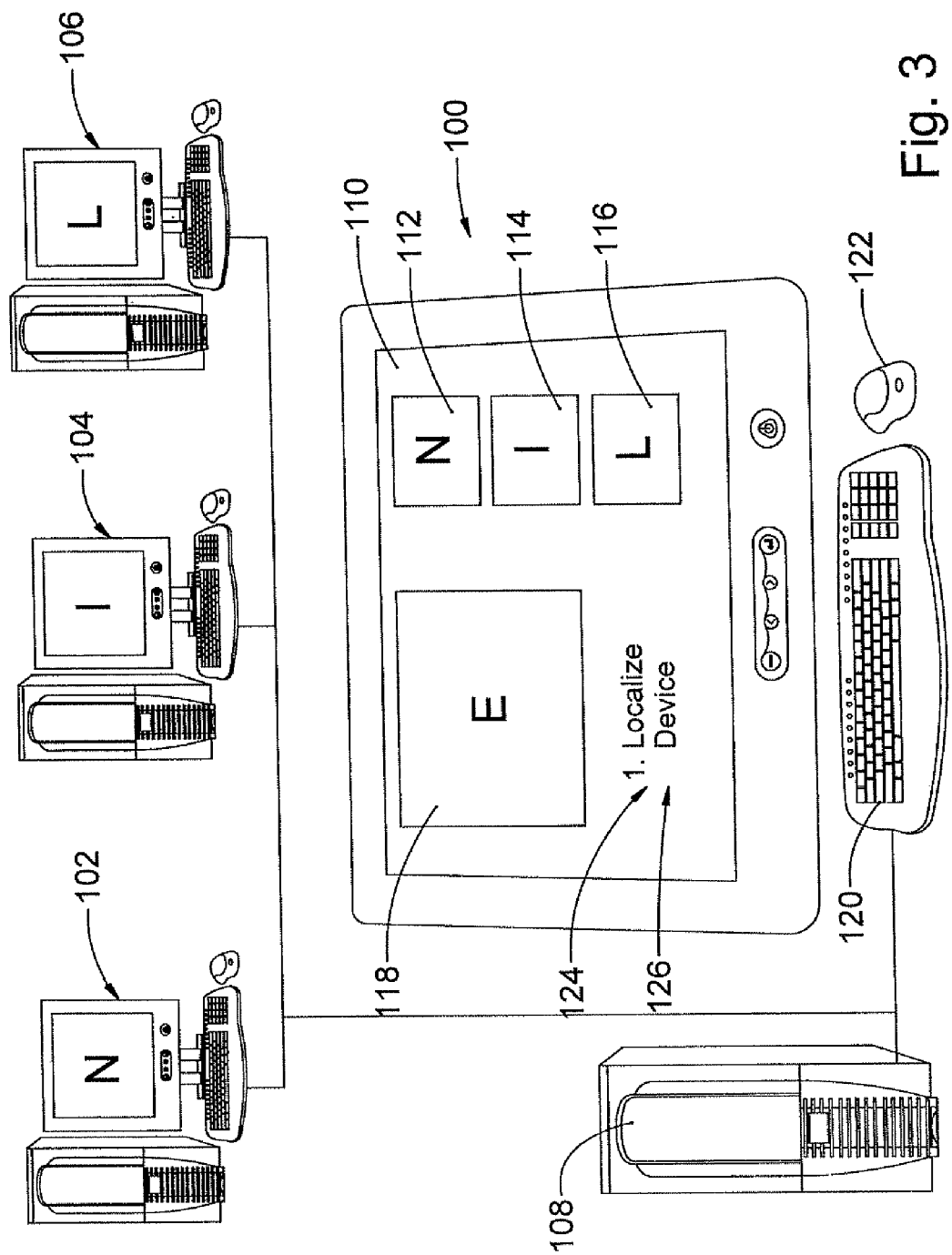
FIG. 3 is a schematic view of a preferred embodiment of a consolidated user interface for performing multistep medical procedure utilizing a plurality of separate medical systems.

A second embodiment of a consolidated user interface in accordance with the principles of this invention is indicated generally as 100 in FIG. 3. The system 100 is adapted for operating a plurality of separate medical systems in order to conduct a medical procedure. As shown in FIG. 3, the system 100 can be used to coordinate and control multiple separate pc-based medical systems, a medical navigation system 102 for orienting and/or advancing a medical device in an operating region in a subject, a medical localization system 104 for determining the position and/or orientation of the medical device in the operating region; and an imaging system, such as an x-ray imaging system, for imaging the operating region. Of course, additional or different PC-based medical systems could be controlled by the system 100. Furthermore, the separate medical systems do not have to be PC-based, and could be controlled by some other type of computer. However each of the separate medical systems preferably accepts user inputs via input devices such as keyboards, mice, track balls, etc., and preferably generates an associated visual display.

Each of the separate systems 102, 104, and 106 are operatively connected to the CPU 108 of the system 100. This connection can be a dedicated wire or wireless connection, or connection via a network. The CPU 108 is programmed to display the associated displays of at least two of the separate medical systems on a composite display 110. The composite display 110 is preferably a single display, such an LCD flat panel display, a CRT display, a plasma display, or a projection display. However, the composite display could comprise a plurality of separate displays that are associated together in a manner for convenient viewing by users.

As shown in FIG. 3, the composite display 110 has a portion 112 for displaying the associated display of the navigation system 102, a portion 114 for displaying the associated display of the imaging system 104, and a portion 116 for displaying the associated display of the localization system 106. These portions 112, 114, and 116 can be dedicated to displaying the associated display of a particular system, or they can be dynamically assigned. The composite display 110 may also include a portion 118 for prominently displaying the associated display of a selected separate medical system.

The system 100 also includes input devices, such as a key board 120 and mouse 122 for operating the system and selectively controlling the separate medical systems. Other input devices can be provided in addition to, or instead of, the key board 120 and mouse 122.

In this preferred embodiment the CPU is also programmed to sequentially display prompts 124 for at least some of the steps of a multistep medical procedure on the composite display 110. These prompts 124 can be a detailed description of the step, or a more abbreviated message recognizable to the user. The prompts can include text or symbolic characters, and are preferably displayed on a dedicated portion or window 126 on the composite display.

Figure 9A:
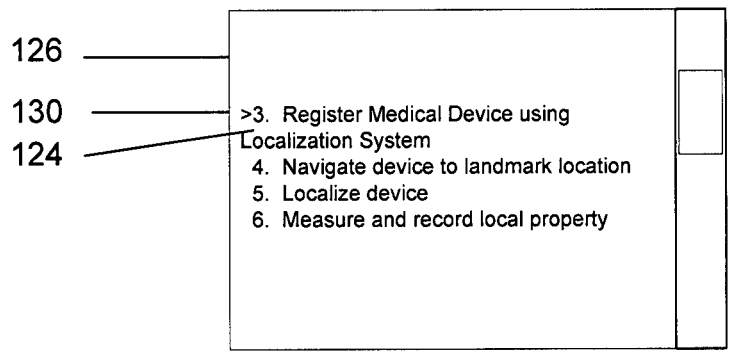
FIGS. 9A, 9B and 9C are schematic diagrams illustrating possible implementations of the prompts that are displayed on the composite display.
Figure 9B:
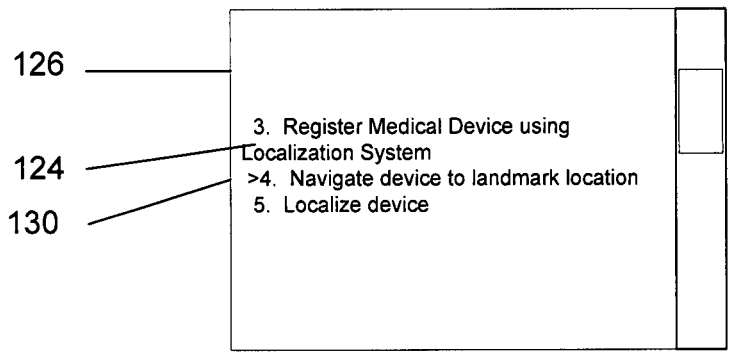
Figure 9C:
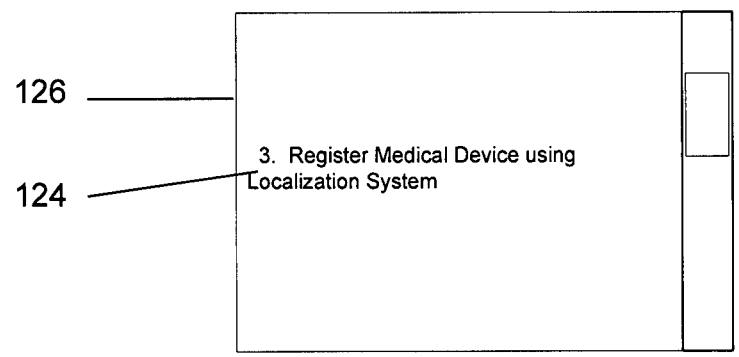

The system 100 can display all of the prompts 124 simultaneously, or a subset of the prompts (FIG. 9A, 9B), for example the current prompt, and the immediately preceding and immediately succeeding prompt (FIG. 9B), or even just a single prompt (FIG. 9C). As shown in FIG. 9, the user may be able to scroll through the prompts, for example with a conventional display scroll bar 128, or the system may advance through the prompts automatically, for example in response to detecting that a step has been completed, or in response to the user indicating through user interface means that a step has been completed. Where more than one prompt is displayed, the system preferably also provides some indicator of the current step, for example with a special character, such as an arrow 130, or by displaying the prompt in a different appearance (such as a difference size, color, or brightness) as shown in FIG. 9B.

Figure 4A:
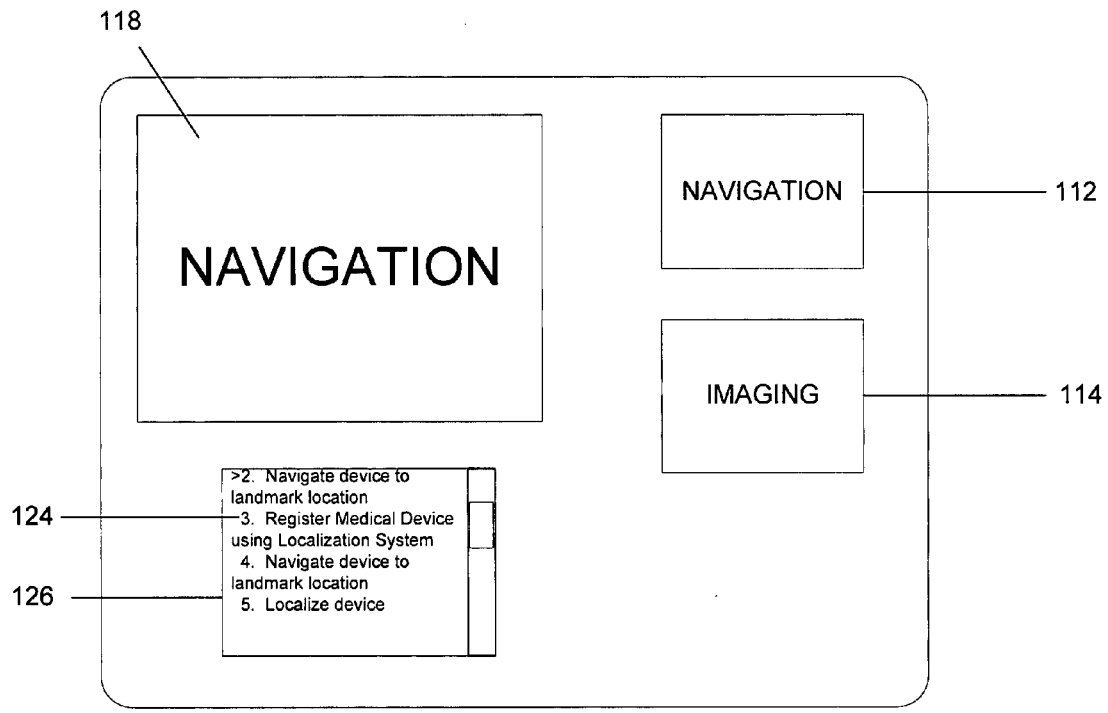
FIGS. 4A and 4B are schematic diagrams illustrating one possible method of highlighting the display from a separate medical system on the composite display.
Figure 4B:
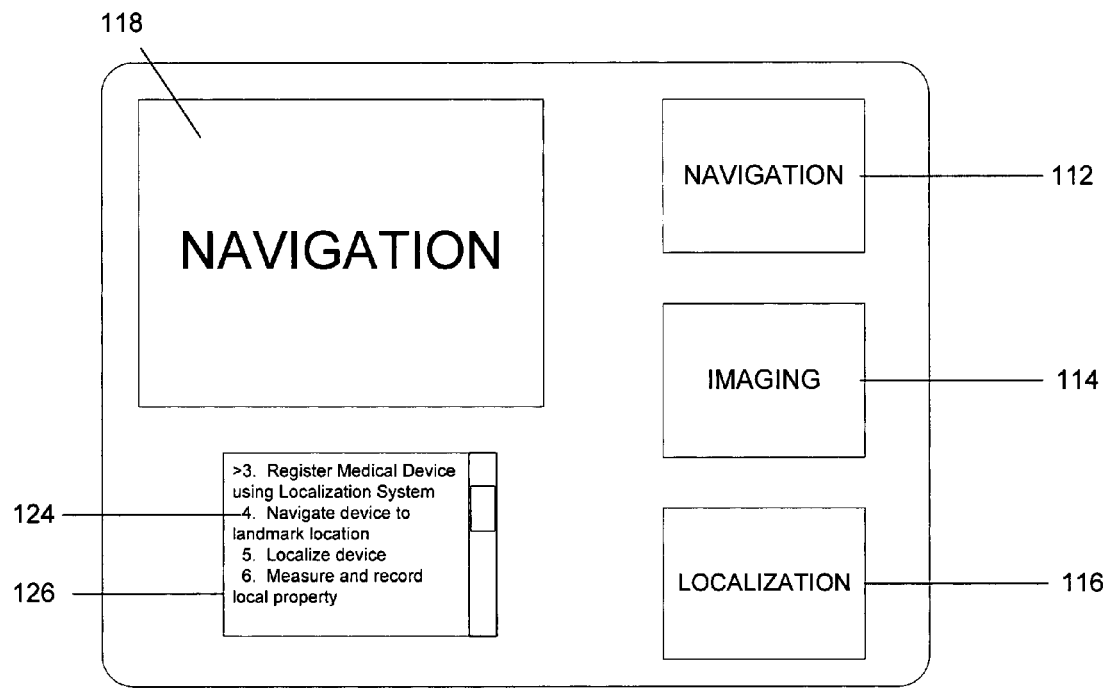

The CPU 108 is preferably programmed to automatically change the composite display 110 if completing the currently prompted step involves use of one of the separate medical systems. This change in the composite display 110 can take many forms. For example, it can be adding the display of the involved computer controlled medical system to the composite display as is shown FIGS. 4A and 4B. In FIG. 4A, the associated display of the localization system is not displayed on the composite display. In FIG. 4B, when the prompt 124 calls for the use of the localization system, the associated display of the localization system is displayed at 116, to facilitate the use of the localization system.

Figure 5A:
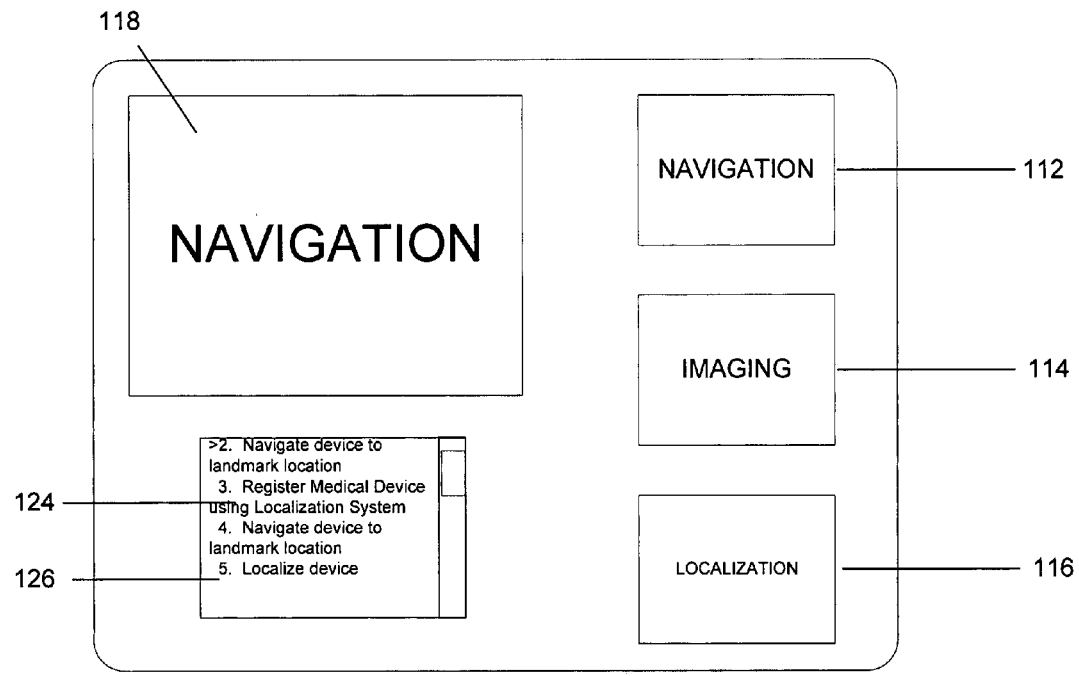
FIGS. 5A and 5B are schematic diagrams illustrating one possible method of highlighting the display from a separate medical system on the composite display.
Figure 5B:
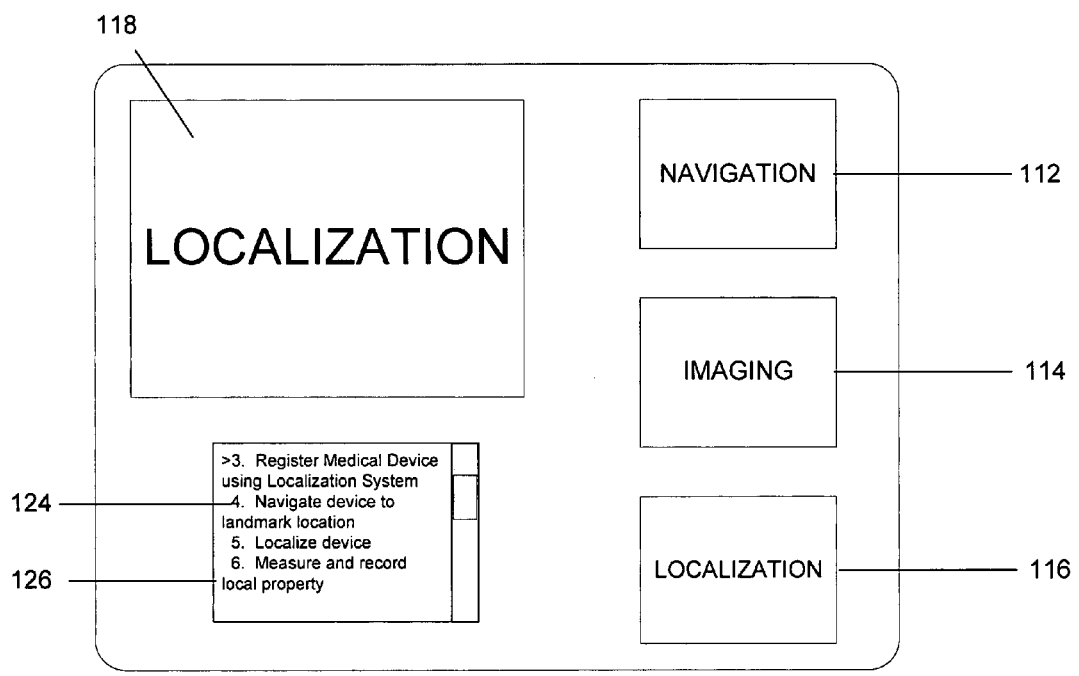

Alternatively the CPU can be programmed to highlight the display of the involved computer controlled medical system if it is already being displayed on the composite display 110. Highlighting the display of the involved computer controlled medical system can be accomplished by displaying the associated display of the involved computer controlled medical system in a prominent location, as shown in FIGS. 5A and 5B. In FIG. 5A, the associated displays of the navigation system, the imaging system, and the localization system are all displayed on the composite display 110. In FIG. 5B, when the prompt 124 calls for the use of the localization system, the associated display of the localization system is displayed on the prominent portion 118 of the display 110, replacing the associated display of the navigation system.

Figure 6A:
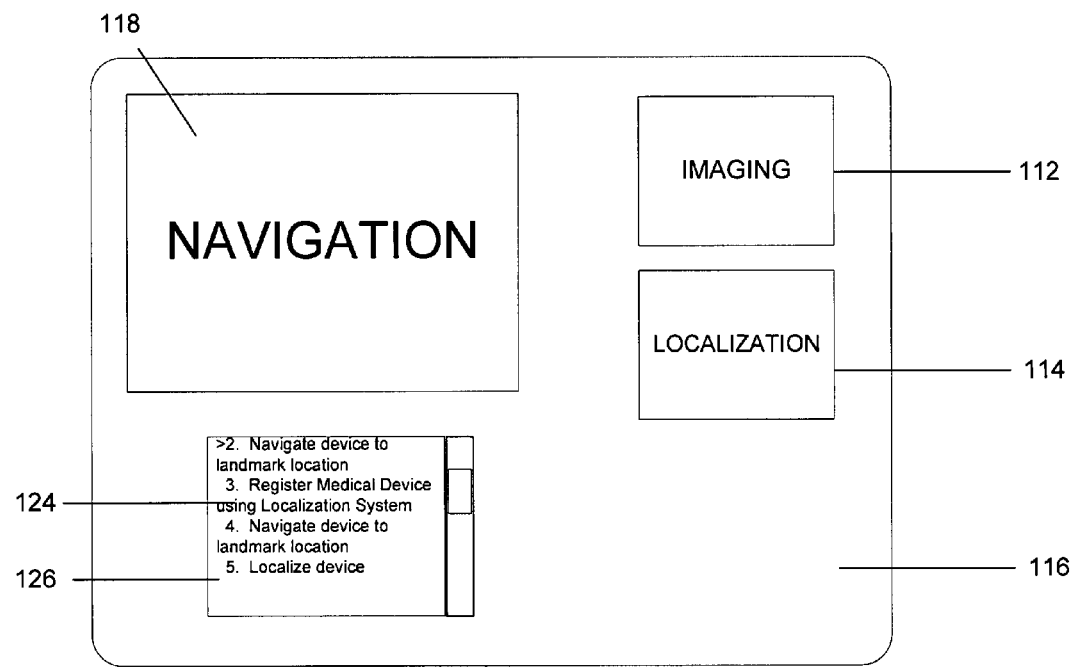
FIGS. 6A and 6B are schematic diagrams illustrating one possible method of highlighting the display from a separate medical system on the composite display.
Figure 6B:
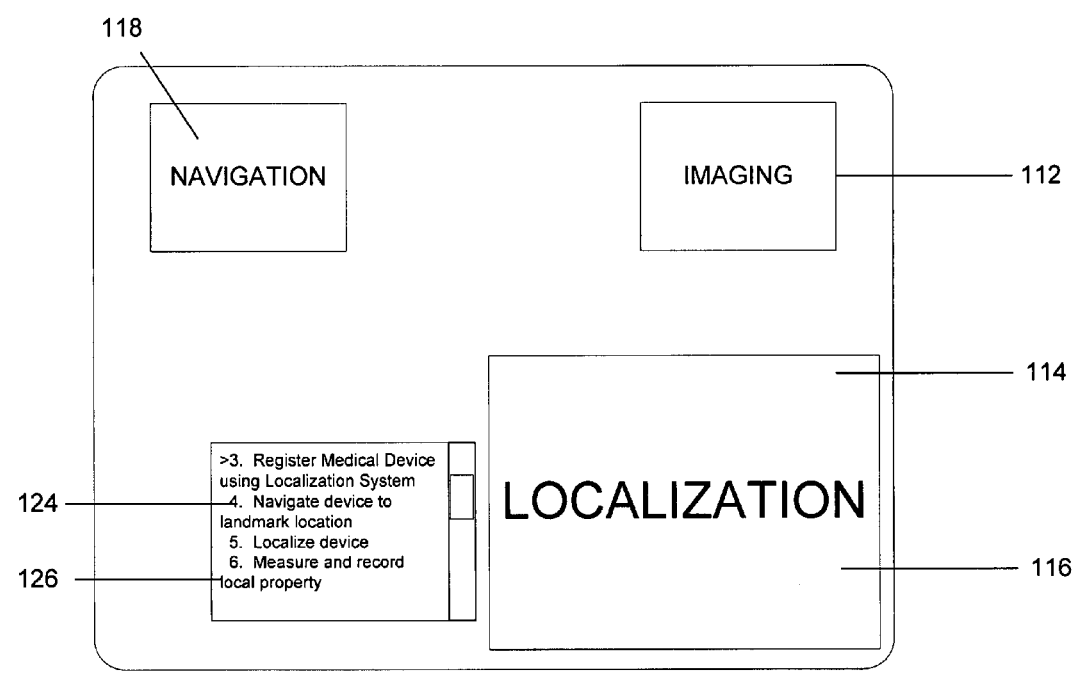

Alternatively, highlighting the display of the involved computer controlled medical system can be accomplished by resizing the associated display of the involved medical system as shown in FIGS. 6A and 6B. In FIG. 6A, the associated displays of the navigation system, the imaging system, and the localization system are all displayed on the composite display 110, with the associated display of the navigation system being enlarged to facilitate the use of the navigation system. In FIG. 6B, when the prompt 124 calls for the use of the localization system, the associated display of the localization system is enlarged to facilitate the use of the localization system.

Figure 7A:
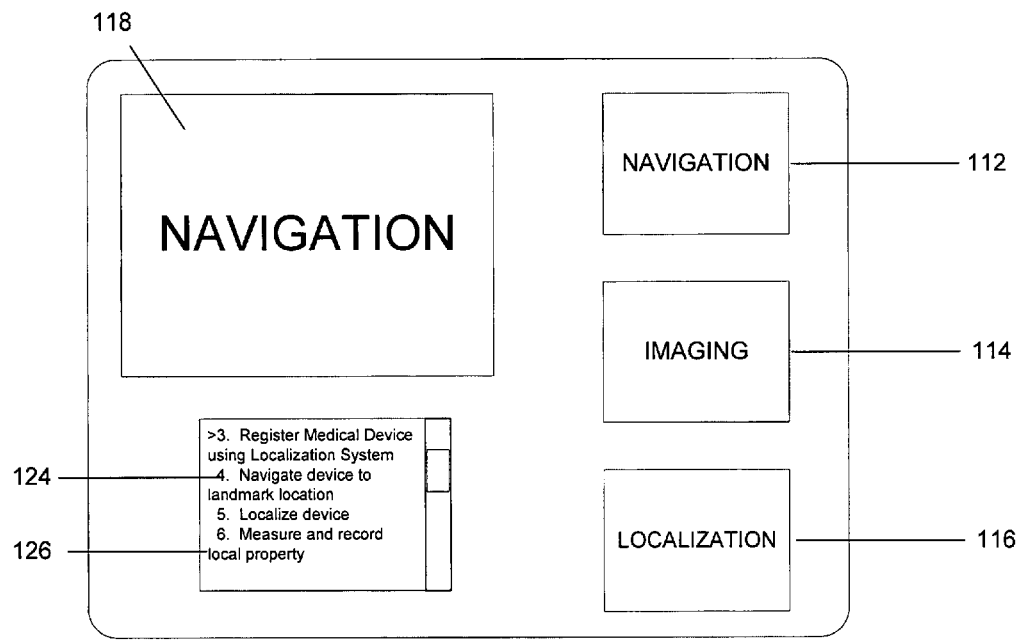
FIGS. 7A and 7B are schematic diagrams illustrating one possible method of highlighting the display from a separate medical system on the composite display.
Figure 7B:
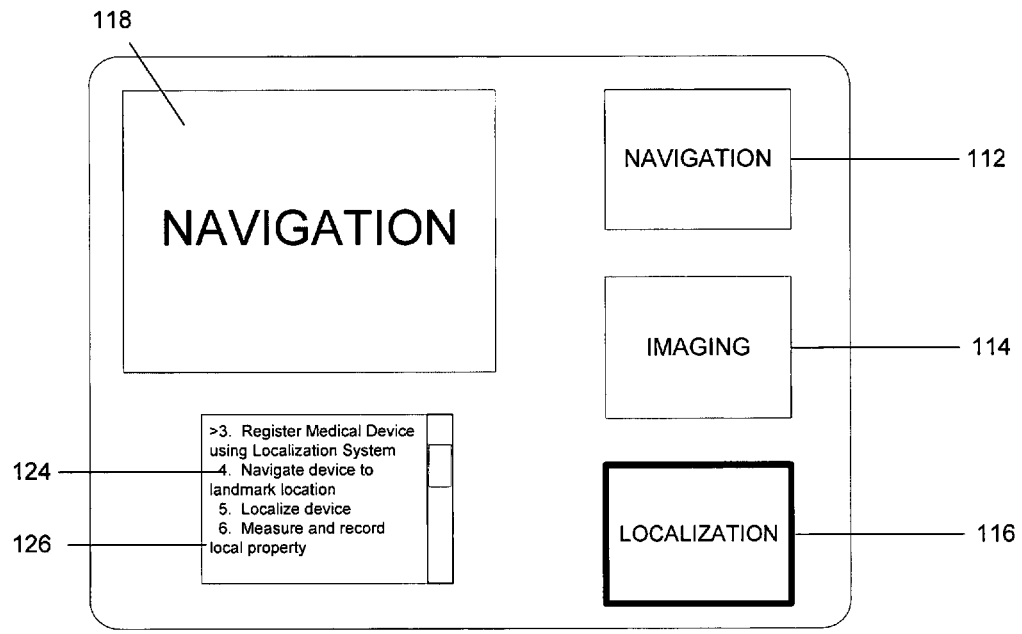

Alternatively, highlighting the display of the involved computer controlled medical system can be accomplished by applying a border or other indicator to the associated display of the involved medical system as shown in FIGS. 7A and 7B. In FIG. 7A, the associated displays of the navigation system, the imaging system, and the localization system are all displayed on the composite display 110, with the associated display of the navigation system having a prominent border. In FIG. 7B, when the prompt 124 calls for the use of the localization system, a border is displayed around the associated display of the localization system.

Figure 8A:
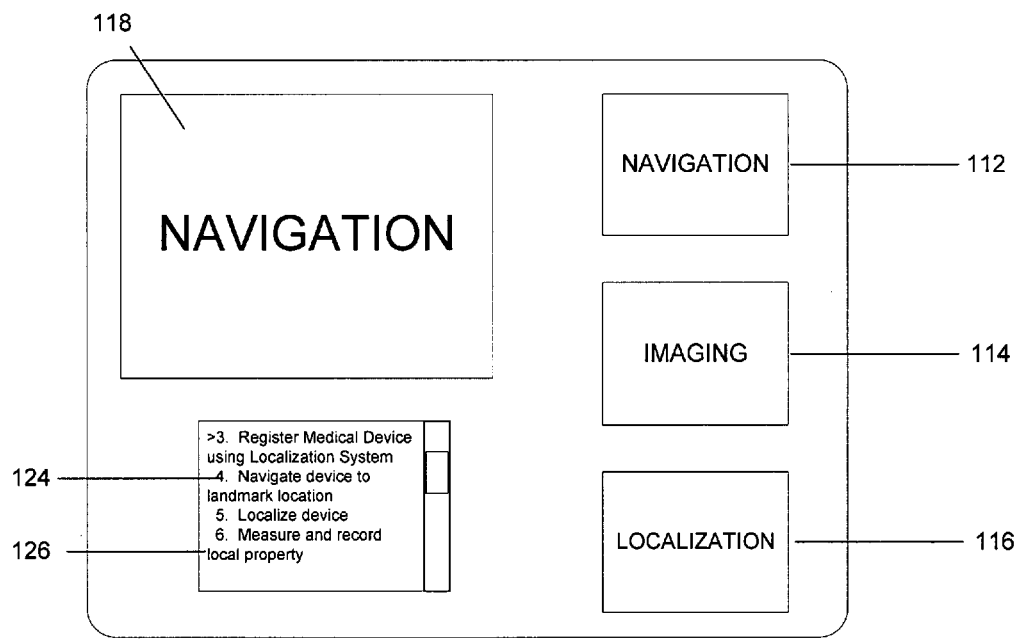
FIGS. 8A and 8B are schematic diagrams illustrating one possible method of highlighting the display from a separate medical system on the composite display.
Figure 8B:
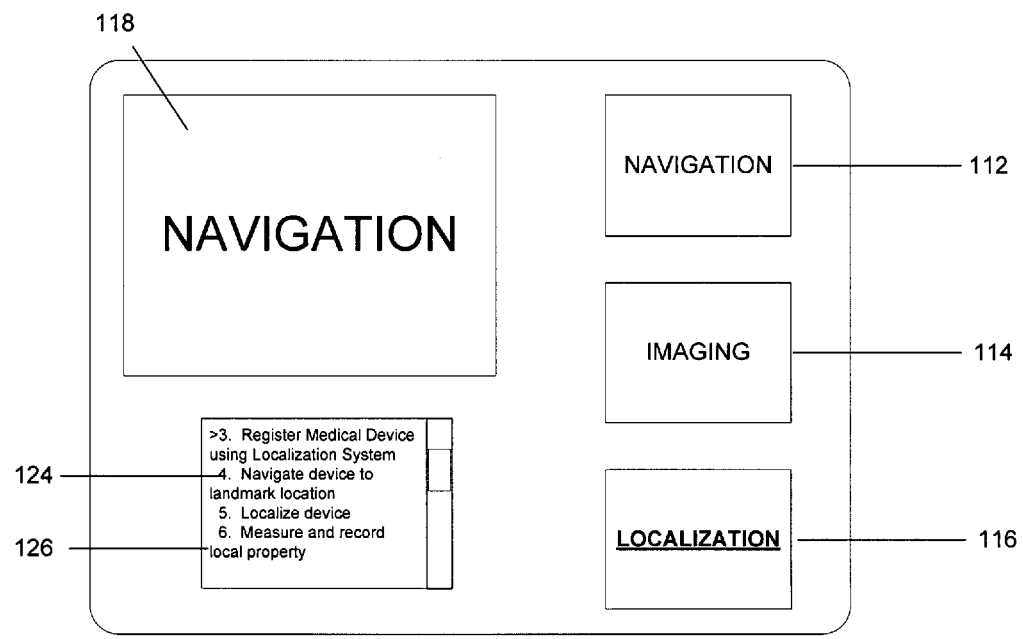

Alternatively, highlighting the display of the involved computer controlled medical system can be accomplished by changing the color or brightness of the involved medical system as shown in FIGS. 8A and 8B. In FIG. 8A, the associated displays of the navigation system, the imaging system, and the localization system are all displayed on the composite display 110, In FIG. 7B, when the prompt 124 calls for the use of the localization system, the intensity of the associated display of the localization system is increased.

Of course some other manner of highlighting can be used, the highlighting serving to quickly identify to the user, the display from the medical system that is involved in the current step, and/or facilitating the use of the display from the medical system that is involved in the current step.

Figure 10A:
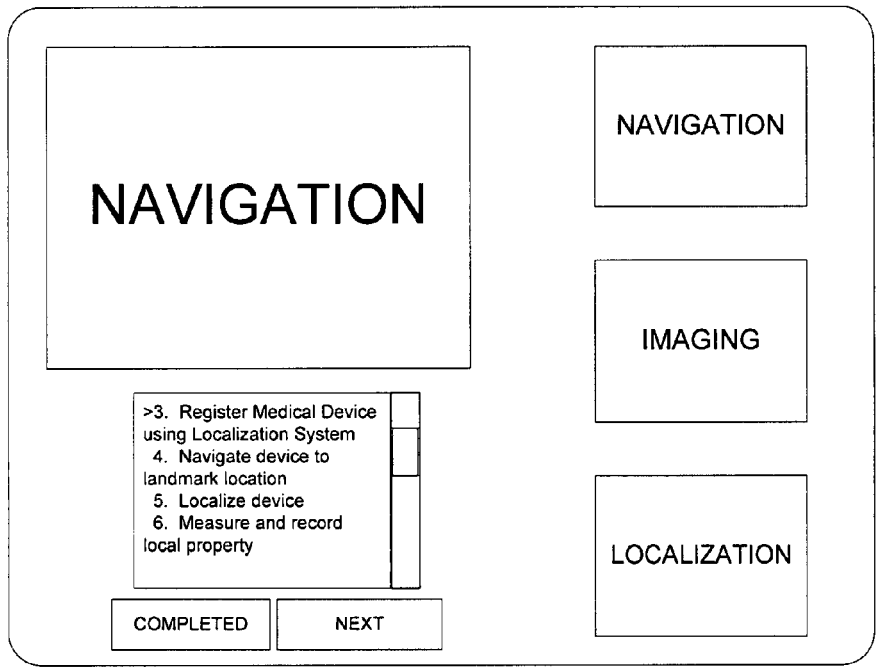
FIG. 10A is a schematic diagram of a display showing control buttons for scrolling through prompts through the workflow.
Figure 10B:
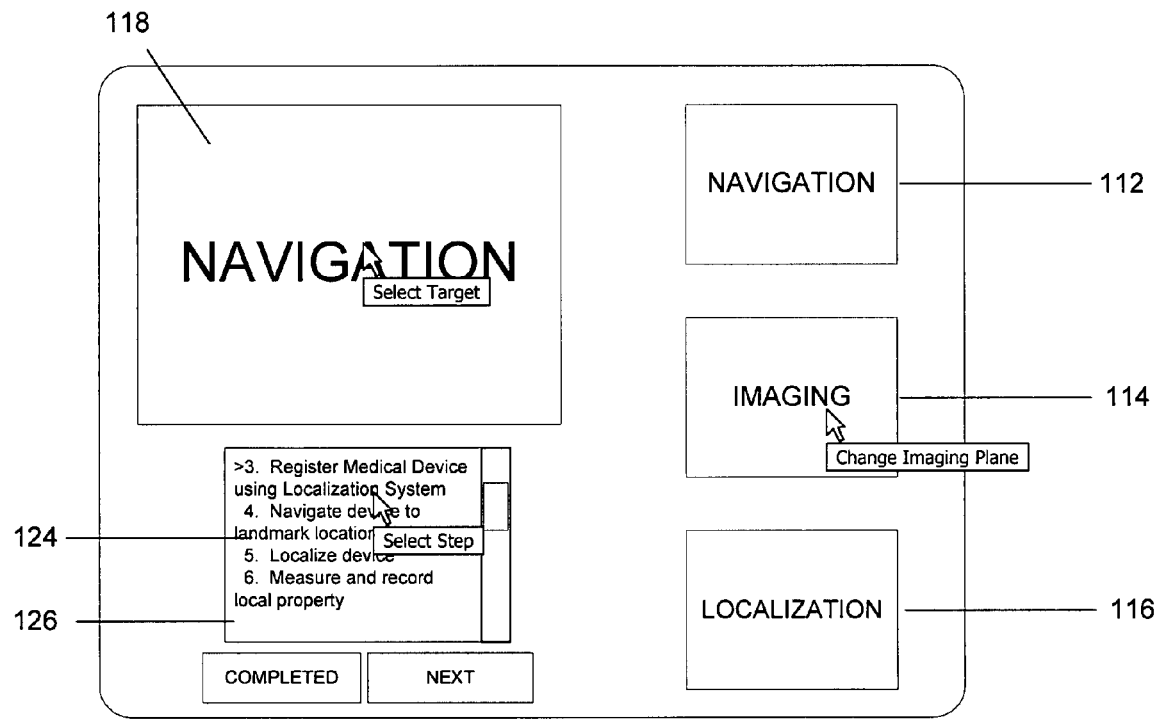
FIG. 10B is a schematic diagram of a display showing an example of the change of appearance of the cursor.

The system 100 may be able to automatically detect the completion of the step associated with the prompt of the current step, and automatically advance the prompt. Alternatively, the user can operate a "completed" 130 or "next" 132 control (FIG. 10) to cause the system 100 to display the prompt for the next step. The prompts can be predetermined for a selected procedure, and for example recalled from memory or storage. Alternatively, the prompts can be dynamically generated based at least in part from user commands, and/or inputs from the various medical systems. Thus, for example the system 100 might present the user with two or more alternatives, and the user can select one of the alternatives using selection buttons 134. The system 100 may also make the appropriate selection for the user, and display just the appropriate selection based in part on user inputs and/or inputs from the various medical systems.

In the preferred embodiment the composite display 110 is configured so that the input devices control a single displayed cursor, and wherever the displayed cursor is located, the input devices, such as the key board and mouse, can be used to operate whatever system is associated with the display over which the cursor is positioned. Thus, by manipulating the input devices the user can move the cursor over then entire composite display 110, and when the cursor is positioned over the portion displaying the associated display of one of the separate medical systems, the input devices can be used to operate that medical system. In this embodiment, more than one of the medical system displays on the composite system is active. The assignment of the input device or computer mouse position to the appropriate medical system is performed by the controller processor, which scales the mouse cursor movement over the composite display based on the current absolute mouse position so as to seamlessly tie the mouse to the appropriate medical system display on the composite display. The controller unit assigns, routes and feeds a corresponding USB output to the appropriate medical system computer. In this manner a single display (the composite display 110), and a single set of input devices (the keyboard and mouse) can be used to control the navigation system, imaging system, localization/mapping system, and so on, independently of the separate displays and separate individual input devices of those systems.

Thus embodiments of the methods and apparatus of this invention provide a way for a user to operate a plurality of separate computer systems, by displaying the displays from each of a plurality of separate computer systems on a composite display; and operating a cursor control device to manipulate a cursor on the composite display (including on the displays of the separate computer systems), and operating the cursor control to operate the separate computer system whose display corresponds to the location of the cursor on the composite display. The cursor manipulated on the composite display may change appearance when it is positioned over at least a subset of the displays of the separate computer systems.

In accordance with another embodiment of this invention, a control can be provided for operating a plurality of separate computer systems. The control comprises a composite display; a video system for receiving display input from each of the plurality of separate computer systems and displaying it on the composite display; a processor; a distribution system connected to the processor and to each of the separate computer systems, and a cursor control device connected to the distribution system, the distribution system receiving input from the cursor control device and communicating the input to the processor, and communicating cursor control input generated by the processor to at least one of the separate computer systems when the cursor on the composite display is on the display corresponding to that separate computer system.

In accordance with another embodiment of this invention, a method of operating a plurality of separate computer systems is provided. The method comprises displaying the separate displays from each of the plurality of separate computer systems on a composite display; translating inputs generated by the operation of a cursor control device to control signals to an interface computer to move a cursor in the interstices between the separate displays on the composite screen and to control signals to the separate computer systems to operate the separate computer systems, so that the cursor appears to operate substantially continuously across the entire composite display, and when the cursor is positioned over the separate display of one of the separate computer systems, the cursor control device operates the separate computer system. In the preferred embodiment the step of translating inputs generated by the operation of a cursor control device to control signals to an interface computer and to control signals to the separate computer systems includes communicating the signals using the USB protocol.

In accordance with another embodiment of this invention, a method of operating a plurality of computer systems is provided. The method comprises translating inputs generated by the operation of a cursor control device to control signals to a first computer to operate the first computer, and generating and transmitting cursor control signals to operate at least one other computer system to operate the at least one other computer system in a corresponding manner. In the preferred embodiment the step of generating and transmitting cursor control signals to at least one other computer systems comprises generating control signals that are different from the control signals for the first computer. The step of generating and transmitting cursor control signals to at least one other computer systems comprises communicating signals via USB protocol.

In accordance with another embodiment of this invention, a method of controlling multiple computer systems running programs with complimentary actions is provided. The method comprises accepting inputs from the operation of a cursor control device and operating a first computer in accordance with the accepted inputs to achieve a desired action, and translating the inputs to a second set of inputs to cause at least one other computer to perform a complimentary action. In the preferred embodiment, the inputs are translated into USB inputs that cause the least one other computer to perform the complimentary action.

One method of accomplishing this is mapping one or more mouse actions on a first computer system (for example operating a particular feature) with a corresponding or complementary action (for example operating the same or a related feature) on at least one other computer system. When one of the mapped actions on the first computer system is performed, the system can automatically generate artificial mouse commands to at least one other computer system to cause that computer system to take a corresponding action. For example a medical navigation system can have a user interface in which the display can be oriented in any of several directions, by pointing and clicking on the control on the display for the medical navigation system. The corresponding controls for orienting the displays from the medical imaging system and the medical localization system can be mapped to the appropriate controls on the navigation system, so that when the user moves a cursor on the display for the navigation system and clicks, artificial mouse commands are generated for the imaging and localization systems to cause their respective cursors to point to a corresponding control and click, without requiring the user to move the cursor and click in each of these systems. In this way, by pointing and clicking in the display of just one of the systems, corresponding actions in the other systems can be taken so that all of the displays are oriented in the same manner. Depending upon the mapping, pointing and clicking on a display of one of the systems on the composite display can cause the same action or a related action to be taken by the other systems.

In another embodiment of this invention a method of performing a medical procedure using a plurality of medical systems controlled by separate computer systems, in which at least some of the computer systems have complementary actions, is provided. The method comprises operating a cursor control device to cause a first computer system to perform a desired action; and generating a cursor control signal to cause at least one other computer system to perform a complementary action. The step of generating a cursor control signal preferably includes using a look-up table to determine the cursor control signal for the at least one other computer system that causes a complementary action to the action performed by the first computer system. This complementary action can be a corresponding action, so that the systems perform the same action, or a coordinated action, so that the systems operate together when commands are made on one of the systems. In specific embodiments, the coordinated actions are at least in part dependent upon the selected intervention workflow.

In another embodiment of this invention, an integrating control and display system for operating a plurality of separate computer systems is provided. The integrating control comprises a master display integrating the separate displays from each of a plurality of separate computer systems; and a cursor control device for manipulating a cursor on the master display (including on the displays of each of the separate computer systems on the master display). The cursor control device operates the system corresponding to the separate display on which it appears on the master display. This allows the user to manipulate a cursor over a single composite display using a single control device, and to control any of a plurality of different computer systems whose displays are displayed on the composite display.

This is preferably achieved using USB protocol so that the systems can be connected without the need for any modification to the system or its programming. Thus, in another embodiment of this invention, a method of operating a plurality of separate computer systems without altering the hardware or software of the separate computer systems is provided. The method comprises: displaying the separate displays of each of the plurality of separate computer systems on a composite display of a master computer system; and operating the cursor control device of the master computer system to manipulate a cursor on the master display, and when the cursor on the master display overlies the separate display of one of the separate computer systems, generating cursor control signals to operate the separate computer system corresponding to the operation of the cursor control device of the master system. The generated cursor control signals are preferably USB cursor control signals for operating the separate computer system.

In another embodiment of this invention, a method of controlling a plurality of separate computer systems is provided. The method comprises displaying the display from each of the separate computer systems on an integrated display; accepting inputs form a cursor control device to move a cursor control device across the integrated display. The cursor control being operable to operate the separate computer system over which the cursor is displayed on the integrated display.

In another embodiment, a system for controlling a plurality of separate computer systems via a master computer is provided. The system comprises a master computer, including a processor, display for displaying a display output from the master computer and each of the separate computer systems, and a keyboard for entering instructions to the master computer system. The processor of the master computer system is programmed to generate control signals for each of the separate computer systems based on the keystrokes on the keyboard, at least some of the keystrokes generating control signals for less than all of the plurality of computer systems. The system is preferably configured so that at least one keystroke on the keyboard generates a control signal for only one of the plurality of separate computer signals. This allows a single keyboard to be used to control a plurality of computer systems, while preserving at least one key for dedicated control of a particular computer system, even while the remainder of the keys are controlling other computer systems.

In one embodiment of this invention, a software parser resides on the master computer and interprets command modifiers to decide onto which of the controlled medical system(s) or computer(s) the command is applicable. The command format is modified in accordance with the parser design to un-ambiguously interpret commands, including generic commands such as "rotate image." In one embodiment, the command syntax is such that commands are preceded by a letter, or combination of letters, that uniquely designate control system(s) to be recipient for the issued command. For example, and in the context of FIG. 3, a preceding "N," "I," or "L" would be interpreted as designating respectively the navigation, imaging, or localization system. According to such a specific syntax, grouping of letters could be interpreted as designating the associated controlled systems, i.e. "NI" would send the issued command to both the navigation and the imaging systems. A parser interpreting keyboard sequence thus can direct a command, group of commands ("macro"), to a subset of the controlled systems or computers comprising one or more system(s) or computer(s). Clearly, specific syntax to be used in the context of a complex system include unique identifiers such that, in the example above, the leading letters "NI" would be uniquely decoded and interpreted as described. Such an embodiment enables rapid command issuing and is intuitive to a subset of users familiar with computer technology.

Alternatively or additionally, the parser functions as a "global keyboard." Specific commands or command shortcuts direct active control to one of a plurality of controlled systems. That is, upon the user typing a short keyboard sequence, active control is passed to a specific controlled system as determined by the keyboard sequence contents. In specific implementations, the keyboard inputs also moves the master computer mouse cursor onto the active window as determined by the command parser.

In another embodiment of this invention, a touch screen is provided as part of the master control system user interface. Buttons on the touch screen enable selection of the active system among the plurality of controlled systems. Additionally, buttons on the touch screen are programmed to activate control command macros consisting of at least one command or operation; in specific embodiments, launching such a macro also redirects the master control system cursor to a location on the associated system display to press a button or select a menu item.

In another embodiment of this invention, a method of controlling at least one of a plurality of separate computer systems based upon the operation of a master computer system is provided. The method comprises generating synthesized USB control signals for at least one of the plurality of separate computer systems, in response to the operation of the master computer systems.

Figure 11:
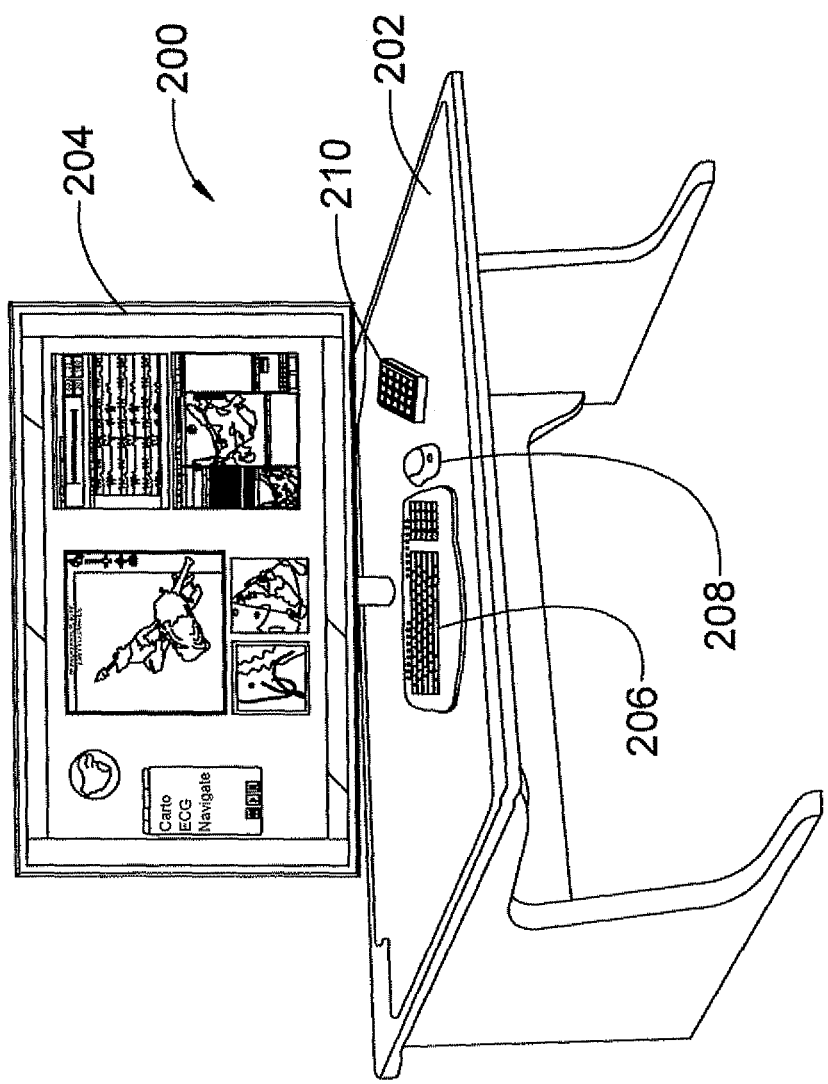
FIG. 11 is a perspective view of one implementation of various embodiments of the systems of this invention.

One possible implementation of several of the embodiments of the invention is illustrated as 200 in FIG. 11, in which a work table 202 is shown with a consolidated display 204, a control key board 206, a control mouse 208, and a dedicated system controller 210 are shown. The consolidated display 204 has a portion 212 for displaying the associated display from a medical navigation system, such as a Stereotaxis magnetic medical navigation system, available from Stereotaxis, Inc., St. Louis, Mo., although the display could be from some other medical navigation system. The consolidated display 204 has a portion 214 for displaying the associated display from a medical imaging system, such as a Siemens x-ray system, although the display could be from some other x-ray system, or from some other type of imaging system altogether, including MRI and ultrasound. The consolidated display 204 also has a portion 216 for displaying the associated display from a medical localization system, such as a Carto localization system, available from Biosense, although the display could be from some other medical localization system. The consolidated display 204 also has a portion 218 for displaying the associated display from an ECG system. The consolidated display 204 can have other portions for displaying the displays from other separate medical systems, and/or some of the portions 212, 214, 216, and 218 could be omitted or replaced.

The consolidated display preferably also includes a window 220 in which prompts 222, preferably generated by the system, guide the user according to a workflow plan. This workflow can be entirely predetermined based upon the type of procedure, or it can be dynamically determined based in part upon selections by the user and/or inputs from the various separate medical systems. In either case the system 200 is preferably set up to automatically reconfigure the composite display 204 for current step in the workflow. The configuration of the composite display 204 for each step can be one that was preset, or it can be one that was modified and saved by the user.

A single cursor is movable on the consolidated display 204 by using the keyboard 206 or mouse 308. The keyboard 206 and mouse 208 are functional to control the separate medical system associated with the portion (e.g. 212, 214, 216, and 218) over which the cursor is positioned. Thus the user can move the cursor from portion to portion by manipulating the keyboard 206 or mouse 208, and when the cursor is in a particular portion of the consolidated display, use the keyboard 206 and mouse 208 to control the associated system. Thus with a single keyboard and mouse, the user can control all of the systems, simply by moving the cursor on the consolidated display 204. A dedicated controller 210 can be provided with buttons or other controls that operate one or more of the separate medical systems regardless of the position of the cursor on the consolidated display. This allows the user to immediately input commands to a system irrespective of the position of the cursor. The dedicated controller can operate just one of the systems, such as the navigation system, or it can have dedicated controls for two or more of the systems. The controls can be dedicated to particular functions, or they can be reprogrammable by the system based upon the context, or by the user, based upon preference.

Alternatively or additionally, a parsing software running on the master controller enables direct use of the keyboard as a means to specify which subset of systems is addressed by a given command. This option for example is available to the user upon moving the master cursor into the master computer text output/input window(s). Alternatively the cursor is automatically moved to the text output/input window upon the user pressing a key or key combinations; such key or key combination being defined for example as a key override mode. Alternatively the cursor is automatically moved to the text output/input window upon the user pressing a combination of mouse buttons or sequence of mouse buttons. In implementations where the system includes a touch screen interface, specific buttons on the touch screen are mapped to activate control command macros; such macros can redirect the master control system cursor to a location on the associated system display to press a button or select a menu item.

Figure 12:
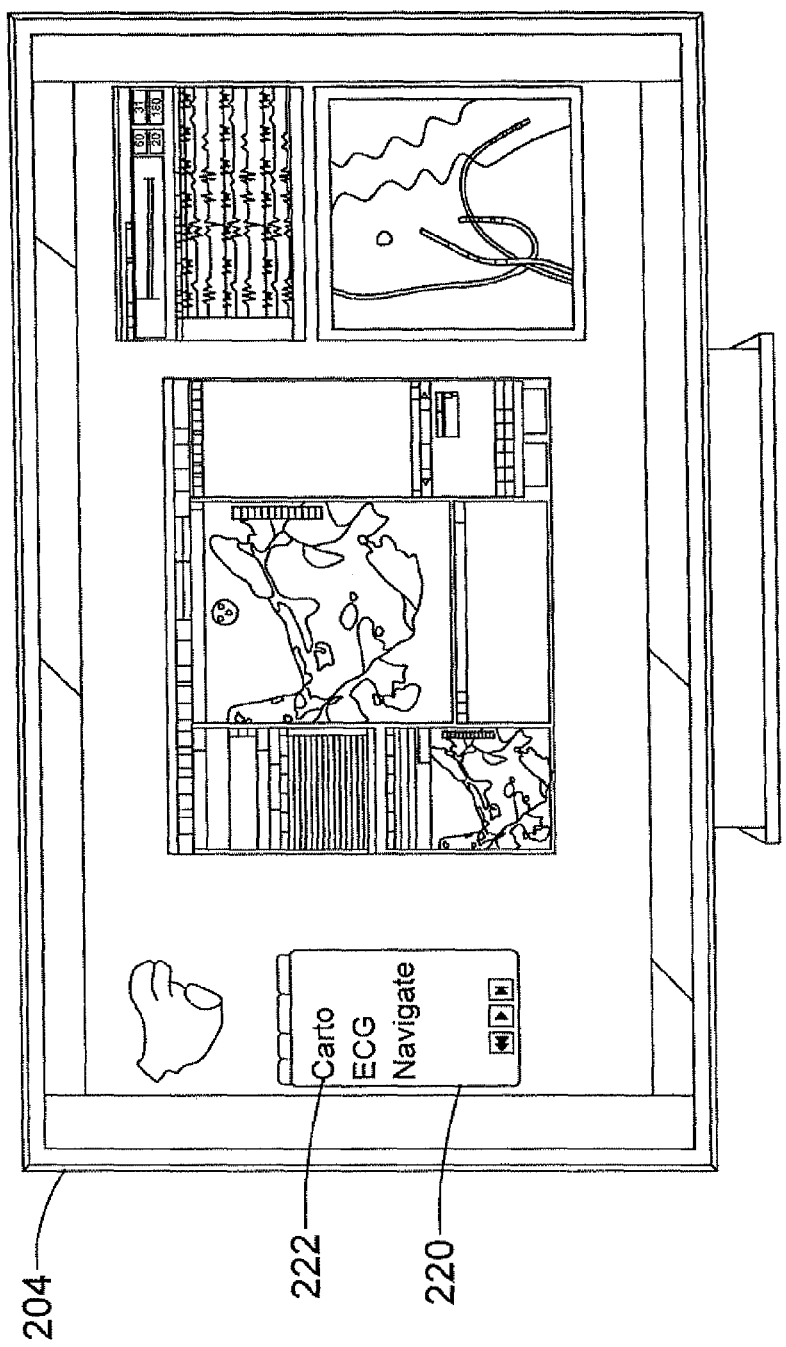
FIG. 12 is a view of a composite display illustrating the reconfiguration of the display in accordance with the workflow.
Figure 13:
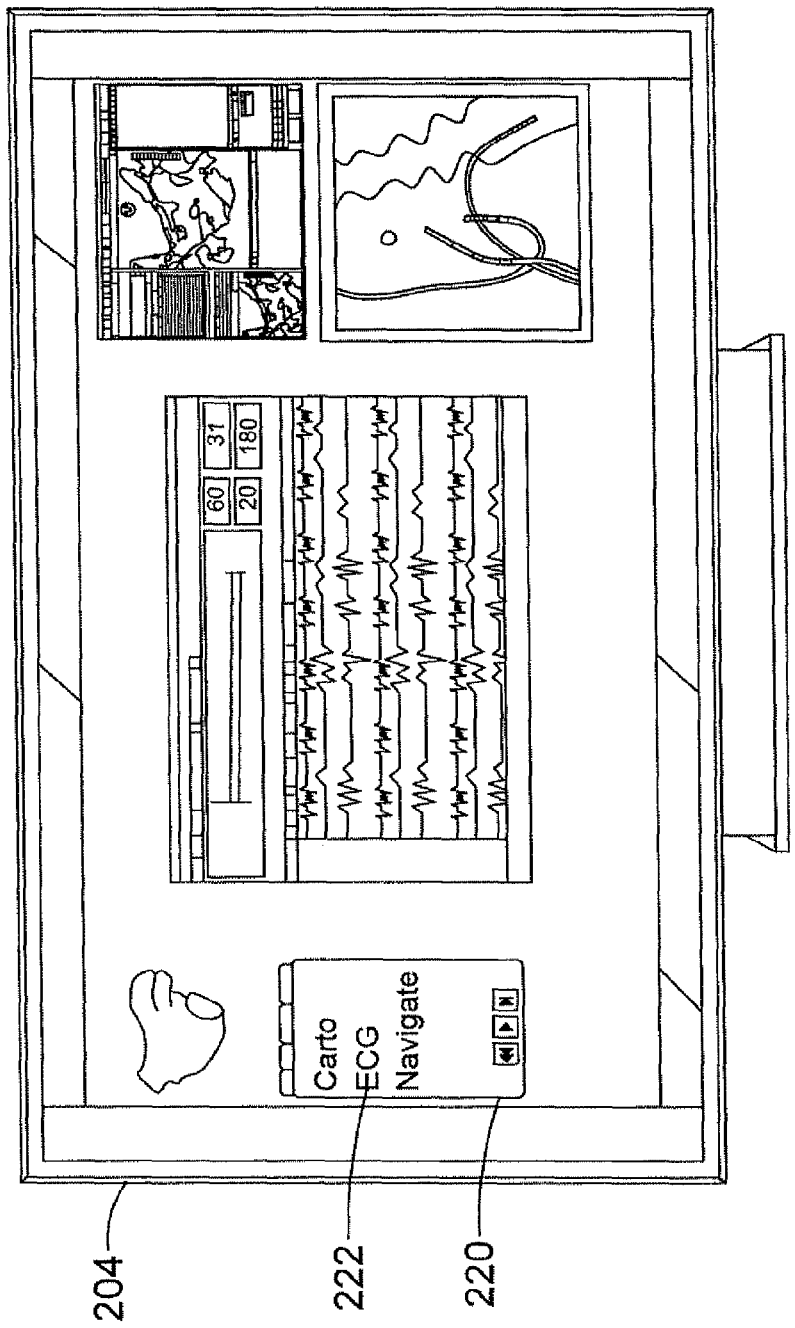
FIG. 13 is a view of a composite display illustrating the reconfiguration of the display in accordance with the workflow.
Figure 14:
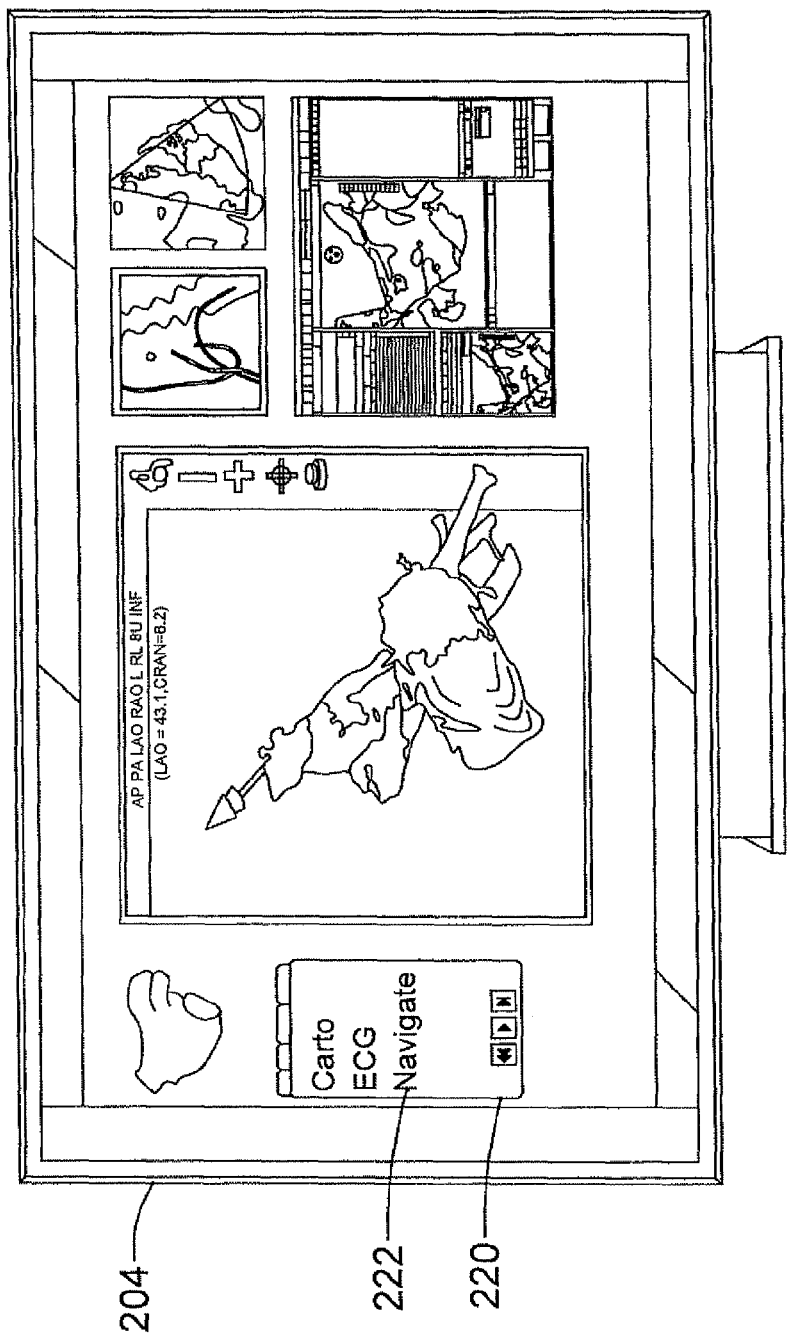
FIG. 14 is a view of a composite display illustrating the reconfiguration of the display in accordance with the workflow.

The operation of the system 200 is illustrated in FIGS. 12-14. In FIG. 12, the Carto prompt 222 is highlighted in window 220, and the composite display 204 is automatically configured for using the Carto localization system. The portion 216 displaying the display form the Carto system is large and centered on the display 204, where it can be easily seen and used by the user. The portions for at least some of the other systems in use are also active on the display, for example portion 218 displaying the ECG display, and portion 214 displaying the display from a medical imaging system. In FIG. 13, the step using the Carto system has been completed, and the prompt 222 to use the ECG system is active in window 220. The composite display 204 is reorganized, with the potion 218 for displaying the ECG display has been enlarged and moved to the center of the display 204, while the portion 216 displaying the Carto display has been resized and moved to the corner, and the portion 214 displaying the display from the imaging system remains unchanged. In FIG. 14, the step using the Stereotaxis navigation system had been completed, and the prompt 222 to use the navigation system is active in window 220. The composite display 204 is reorganized, with the potion 212 for displaying the navigation system display has been positioned in the center of the display 204, portion 214 displaying the display from the imaging system has been moved to the upper right corner of the display, and the Carto system has been moved to the lower right corner of the display.

Figure 15:
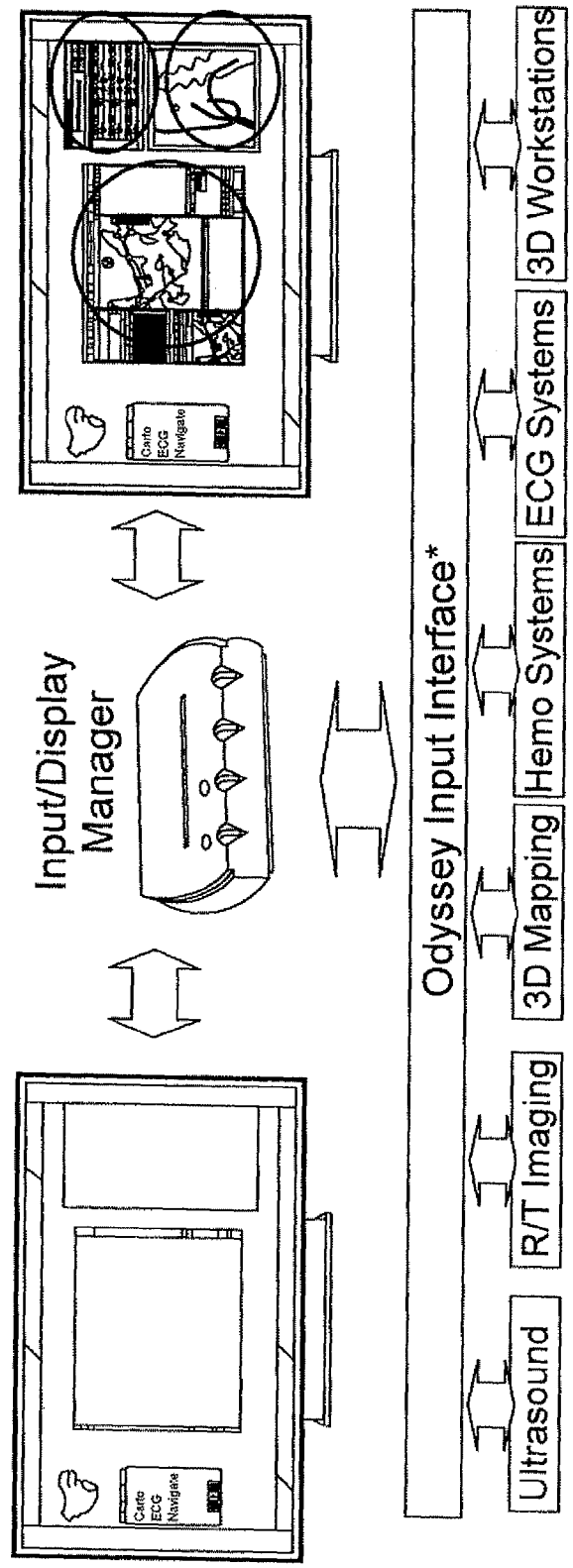
FIG. 15 is a schematic diagram of the architecture of one possible system implementing various embodiments of this invention.

A possible architecture of the system is shown in FIG. 15. As shown in FIG. 15, a plurality of separate systems interface with an input/display manager. These systems can include, for example, an ultrasound system, a real time imaging system, a 3D mapping system, a Hemo system, an ECG system, and a 3D workstation. The input/display manager directs which of the displays of the various systems get displayed on the composite system, and manages their size and location, all in accordance with the workflow, automatically updating the composite display each to the configuration appropriate for each step in the work flow.

Regardless of the configuration, the user can control any of the systems displayed simply by moving the cursor over the appropriate portion of the composite display, and operating the graphical user interface of the system with the mouse and keyboard.

Figure 16:
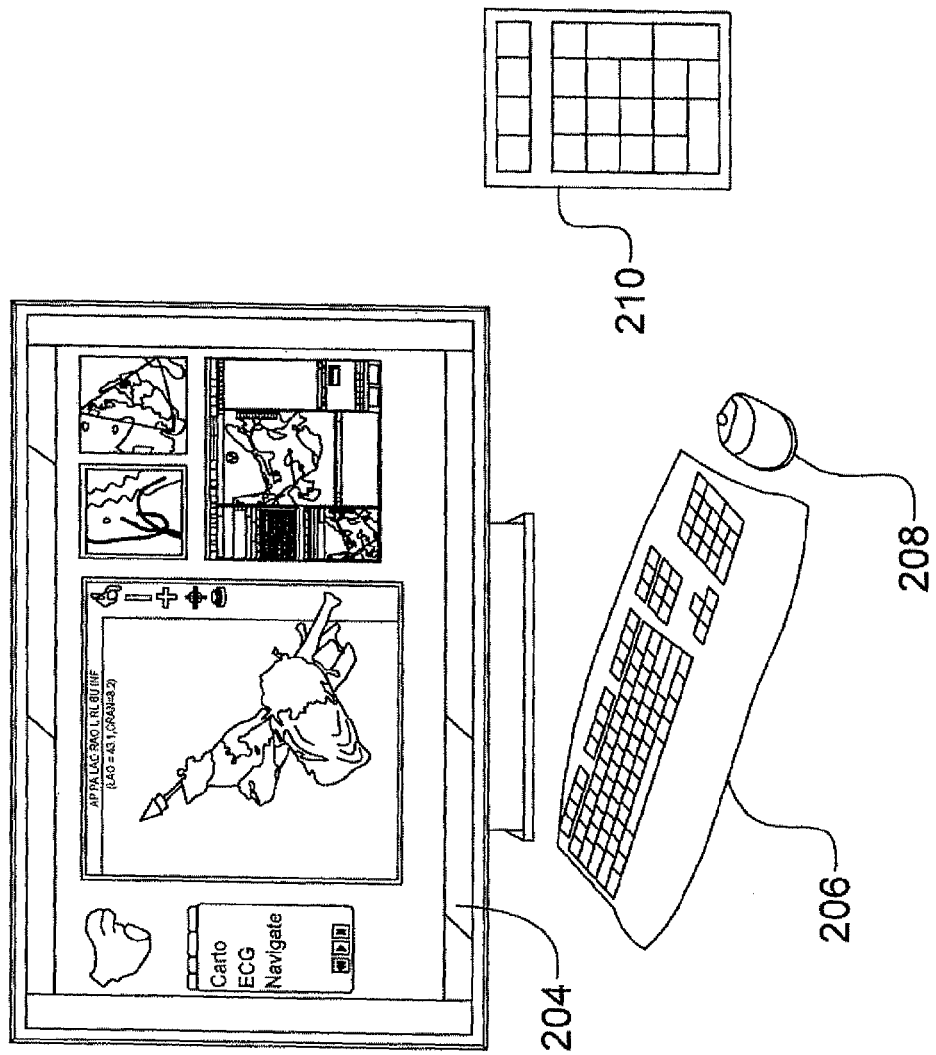
FIG. 16 is a schematic diagram of some of the components of a possible system implementing the various embodiments of this invention.
Figure 16:
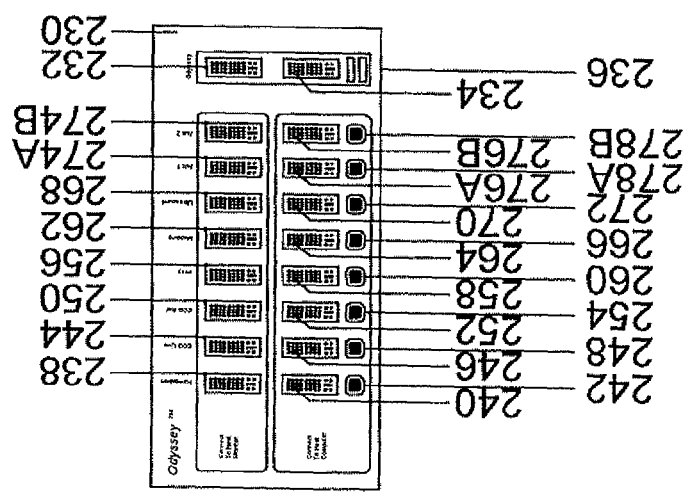
Figure 17B:
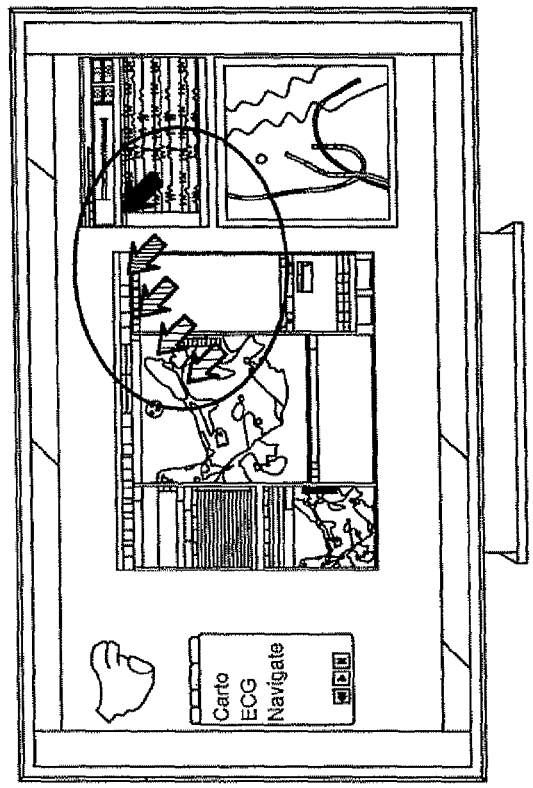
FIGS. 17A and 17B are views of the composite display, illustrating the apparent movement of the a single cursor across the composite display.
Figure 17A:
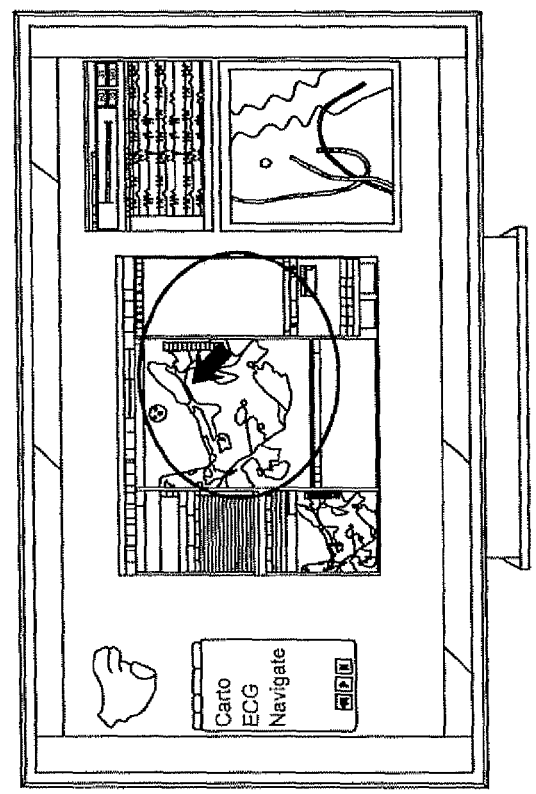

The components of the system 200 are shown schematically in FIG. 16, comprising a composite display 204, keyboard 206 and mouse 208, and dedicated controller 210. The connector plate for the input display manager is indicated as 230 in FIG. 16. The connector plate has a serial port 232 for connecting to the composite monitor 204 and a serial port 234 for connecting to the video card of the computer running the system 200, and a USB connector 236 for connecting to a USB port on the computer running the system 200. In addition the connector plate has a monitor, video card, and USB connections 238, 240, and 242 for the separate navigation system; monitor, video card, and USB connections 244, 246, and 248 for the separate live ECG system; monitor, video card, and USB connections 250, 252, and 254 for the separate reference ECG system; monitor, video card, and USB connections 256, 258, and 260 for the separate x-ray imaging system; monitor, video card, and USB connections 262, 264, and 266 mapping/localization system; monitor, video card, and USB connections 268, 270, and 272 for the separate ultrasound system; two sets of monitor, video card, and USB connections 274 A & B, 276 A & B, and 278 A & B for additional separate computer based medical systems.

This arrangement allows the user to connect separate systems together without modifying the individual systems, and control them from the composite display 204 using the keyboard 206 and mouse 208. The system 200 operates so that the mouse appears to move continuously across the composite display 204 across the portions that represent the displays of the individual systems, where the cursor is actually a cursor moving on the interface of the separate system, and across the portions of the composite display between those portions, where the cursor is the cursor of the interface of the system 200. By managing the cursor in this way, it appears to be a single cursor moving continuously over the display 200, even though it may actually be several cursors.

As shown in FIG. 18, when the cursor appears in a particular portion of the screen, the keyboard 206 and mouse 208 operate to control the separate system in whose display the mouse is visible. Thus in FIG. 18A, the cursor displayed is the cursor in the Carto system, and operating the keyboard 208 operates the Carto system. In FIG. 18B, the cursor has been moved to the portion of the composite display showing the display of the ECG system. This is shown by the solid white cursor arrow, the faded cursor arrows simply showing previous positions of the cursor, illustrating that the movement appears to the user to be continuous, even though in the preferred embodiment it is not continuous (and instead is a series of the separate system cursor arrows bridged by the cursor arrow from the system). In FIG. 18B, since the cursor arrow is in the ECG portion of the display, the keyboard 208 operates in the ECG system.

One embodiment of a seamless multi-system keyboard and mouse controller uses a USB implementation. FIG. 19-A shows a general system diagram for such an embodiment. Master controller 402 receives video inputs 404 from a set of controlled medical systems or computers 401, 403, . . . , 407, and generates a composite video output 406 that is sent to at least one master screen(s) 408. Master controller 402 also provides inputs to electronic controller 410 that redirects command inputs such as test inputs from keyboard 412 to a selected controlled medical system or computer based on current cursor position as determined at least in part by position and movement of mouse 414. Other input signals to electronic controller include mouse clicks and other inputs dependent upon specific UIF configuration(s). FIG. 19-B illustrates details of the electronic circuit that is part of, or associated with, the master medical system or master computer in one example of such an embodiment. In this embodiment, the control system consists of electronic circuits that send appropriate keyboard and mouse events to a controlled system making that system appear to function as one selectable window among many other similarly controlled systems. The electronic control system utilizes standard computer interfaces including Universal Serial Bus (USB) to effect the keyboard and mouse control in such away that the controlled system requires no specialized hardware or software to enable such control. The seamless keyboard and mouse controller consists of a master computer and consolidated display, a control program on the master computer system to arbitrate control events between multiple controlled systems, an electronic circuit 500 for simulating keyboard and mouse interfaces on controlled systems, and firmware programming to translate master control events into standard keyboard and mouse events for the controlled system. The firmware on the electronic controller utilizes a standard Human Interface Descriptor (HID) to allow the simulated mouse and keyboard events to be implemented with no hardware or software modifications of the controlled system. As the operator uses the master control computer, the control software determines which controlled system should be subject to the operator's inputs. The control software then instructs the USB microcontroller 504 corresponding to the selected controlled system(s) to generate simulated keyboard and mouse events directly interpretable by the controlled system, such that controlled system(s) appears to seamlessly function within the context of the master system. The control system further uses a mouse control mode that allows the specific placement of the cursor to be specified by the master system thus allowing the seamless motion of a cursor across many computer systems.

Thus embodiments of this facilitate the control of multiple medical systems with a single, simple interface system.

The consolidated system as described above limits the number of simultaneous keyboard and mouse controls to one. It is possible to retain the native keyboard and mouse of each system connected to the consolidated system; however, these components do not operate similarly to the consolidated system global keyboard and mouse. Instead, these components are limited to control the native system they are directly connected to rather than being capable of operating any system connected to the consolidated system. In another embodiment of this invention, a consolidated user interface is disclosed that controls a multiplicity of medical systems or computers, and a plurality of keyboard and mice combinations can be connected to the consolidated system to support at least two simultaneous controls operating seamlessly with the consolidated display.

In a first embodiment, two or more input devices combinations such as keyboard and mouse are connected to the consolidated system. Each keyboard may initially be set to focus its input on a separate system controlled by the consolidated display (subject to the number of input device combinations being not more than the number of controlled systems). Each keyboard is associated with the system display it's controlling through a graphical indication; one example of such a graphical indication is a colored border around the window and a corresponding colored marker on the keyboard, or alternatively a keyboard of the corresponding color. Several design approaches enable simultaneous control of at least one of a plurality of controlled systems. In one embodiment, the position of each global cursor is indicated with a graphic such as a circle, halo, or similar graphic differentiator presented as an overlay constantly displayed over all windows of the consolidated display. In this manner, as any of the mice is moved, the corresponding global cursor graphic is moved. In a preferred embodiment, the graphic does not block the central area of the global cursor position, so as to allow the native cursor of each system to appear in its center. When the global cursor position of each mouse is located in a distinct associated system window, each mouse controls its associated system independently without interference from any of the other mice; the native cursor of each system appearing in the center of each global cursor position graphic. When the global cursor positions of two or more mice are in the same system window, careful design enables seamless operation without interference. For example, when a first global cursor is in a first system window and a second global cursor is in a second system window, each global cursor begins with the native cursor of the system in the center of the global cursor graphic. When a first mouse is moved to translate a first global cursor to a second system window, the native cursor for the second system disappears from the center of the second global cursor and immediately appears in the center of the first global cursor as soon as it crosses the border into the second system window. In this implementation, the locus of control switches to the latest entrant into the window of the particular system under control. Effectively, only one mouse will control the system at any time even though the global cursor graphics of the two (or more) mice appear in the same window. A list of control priority is maintained for each control window, in such a manner that the first priority is always with the latest entrant cursor, and prior cursor(s) that are still in the window are pushed down the ordered list. Once a cursor leaves a given window, it ceases to be listed in the priority list for that window. Should the latest entrant cursor stop moving, the locus of control returns to the next cursor in the priority list that is moving, which then assumes the first priority in the priority list, and the former "priority" cursor (the cursor having control) moves to the second place on the priority list. Should a second cursor start moving while the priority cursor is still moving, priority remains with the current priority cursor. If none of the cursors is moving, priority remains with the last cursor having priority. Accordingly in such situations the native cursor will always react to the currently moving mouse and in the event two or more mice are concurrently moving, the mouse that initiated movement first maintains control of the native cursor. This priority order is shuffled only by a "new" cursor entering the window; or by the priority cursor ceasing to move and another cursor continuing or resuming motion. The global priority cursor graphic appears with a matching shape or color corresponding to the controlling mouse, and is highlighted by use of a significantly higher intensity, larger shape, or similar differentiator that is not distracting to the users. With this approach, the operation appears nearly the same as having a consolidated system mouse operating in the same window as a native mouse on the same independent system, but enables multi-user workflows from a single large display. In addition, this embodiment of the present invention offers a new level of control for remote proctoring or procedure scenarios. In this manner, a remote proctor or physician can effectively work in tandem with a local user of the system.

What is claimed is:

1. A system for performing a multi-step medical procedure requiring the operation of a plurality of separate computer systems, each accepting inputs and providing a visual display, the system comprising:
   at least first and second composite displays, the first composite display being located remotely from the subject of the procedure, the first and second composite displays each including the visual displays from at least two of the separate computer systems; and
   at least one control for changing the configurations of the first and second composite displays in accordance with the steps in a preplanned workflow, the control being programmed to change the composite displays such that when a step in a multi-step medical procedure calls for use of at least one of the separate computer systems, the composite display displays the visual display of the at least one separate computer system called for in the step, with the configuration of the first and second composite displays being different for at least some of the steps.

2. The system according to claim 1 further comprising a control for displaying a prompt for at least one of the steps in the preplanned work flow on the first and second composite displays.

3. The system according to claim 2, wherein the prompts displayed on the first and second composite displays for at least some of the steps are different.

4. A system for operating a plurality of separate computer systems, each having a visual display, the display comprising:
   a composite display comprising a single display;
   a video system for receiving display input from each of a plurality of separate computer systems that include a navigation system, a localization system and an imaging system, and displaying the associated displays of at least two of the plurality of separate computer systems on the composite display; and
   a processor for controlling a multi-step medical procedure in which some of the steps involve the use of one of the separate computer systems, the processor being programmed to change the composite display such that where a step calls for use of one of the separate computer systems, the composite display prominently displays the associated display of the separate computer system involved in the step; whereby the processor controls the display of the associated displays of the navigation system, a localization system and an imaging system on the composite display based upon a planned multi-step medical procedure.

5. The system according to claim 4, wherein the composite display is a Plasma, DLP or Liquid Crystal Display (LCD).

6. The system according to claim 4, wherein the composite display is generated by one or more video projectors to form a composite display on any suitable surface.

7. The system according to claim 4, wherein the configuration of the composite display is different for at least some of the steps.

8. The system according to claim 4 wherein the processor is further configured to display a prompt for at least some of the steps in the preplanned multi-step medical procedure on the composite display.

9. The system according to claim 8, wherein the prompts displayed on the composite display for at least some of the steps are different.

* * * * *